US011806385B2

United States Patent
Gendelman et al.

(10) Patent No.: US 11,806,385 B2
(45) Date of Patent: Nov. 7, 2023

(54) BIOMARKERS FOR MONITORING IMMUNE TRANSFORMATION

(71) Applicants: Board of Regents of the University of Nebraska, Lincoln, NE (US); The Scripps Research Institute, La Jolla, CA (US)

(72) Inventors: Howard E. Gendelman, Omaha, NE (US); R. Lee Mosley, Omaha, NE (US); Gary Siuzdak, La Jolla, CA (US); Erica Forsberg, San Diego, CA (US)

(73) Assignees: BOARD OF REGENTS OF THE UNIVERSITY OF NEBRASKA, Lincoln, NE (US); THE SCRIPPS RESEARCH INSTITUTE, Jolla, CA (US)

( * ) Notice: Subject to any disclaimer, the term of this patent is extended or adjusted under 35 U.S.C. 154(b) by 215 days.

(21) Appl. No.: 16/092,561

(22) PCT Filed: Apr. 24, 2017

(86) PCT No.: PCT/US2017/029111
§ 371 (c)(1),
(2) Date: Oct. 10, 2018

(87) PCT Pub. No.: WO2017/185085
PCT Pub. Date: Oct. 26, 2017

(65) Prior Publication Data
US 2019/0117735 A1  Apr. 25, 2019

Related U.S. Application Data

(60) Provisional application No. 62/326,062, filed on Apr. 22, 2016.

(51) Int. Cl.
*G01N 33/50* (2006.01)
*A61K 38/19* (2006.01)
*A61K 38/22* (2006.01)
*G01N 33/68* (2006.01)
*G01N 33/94* (2006.01)

(52) U.S. Cl.
CPC ........ *A61K 38/193* (2013.01); *A61K 38/2278* (2013.01); *G01N 33/505* (2013.01); *G01N 33/6896* (2013.01); *G01N 33/942* (2013.01); *G01N 2800/52* (2013.01)

(58) Field of Classification Search
None
See application file for complete search history.

(56) References Cited

U.S. PATENT DOCUMENTS

| | | |
|---|---|---|
| 6,187,756 B1 | 2/2001 | Lee et al. |
| 2008/0131921 A1 | 6/2008 | Myint et al. |
| 2013/0217036 A1 | 8/2013 | Cohen et al. |
| 2014/0140986 A1 | 5/2014 | Santos et al. |
| 2014/0349877 A1 | 11/2014 | Gendelman et al. |
| 2015/0139937 A1 | 5/2015 | Gendelman et al. |
| 2016/0184417 A1 | 6/2016 | Gendelman et al. |
| 2016/0367564 A1* | 12/2016 | Cowley ............... A61K 31/404 |

OTHER PUBLICATIONS

Rowin et al, (Muscle Nerve 46: 449-453, 2012).*
Szabo et al (J Neurol Sc 310: 256-260, 2011).*
Politis et al (Behav Br Res 277: 136-145, 2015).*
Zinger et al (SAGE—Hindawi Access to Parkinson's Disease, vol. 2011, 1-11, 2011).*
Alenov et al (Meditsinskii Zhurnal Uzbekistana (1988), (5), 54-5) (abstract).*
Gendelman et al (J Neuroimmune Pharmacol 11: pp. S3, S61, online publication Mar. 18, 2016).*
Gendelman—Clinical Trial Leukine (Sargramostim) for Parkinson's Disease—Full Text View—ClinicalTrials.gov, Jan. 2015 version, downloaded on Jun. 10, 2023, 9 pages.*
Munn, D.H., et al., "Indoleamine 2,3 dioxygenase and metabolic control of immune responses" Trends Immunol. (2013) 34(3): 137-43.
Kosloski-Bilek, L., "Immune Modulation for Parkinson's Disease" Thesis, University of Nebraska Medical Center (2014) ProQuest LLC, Ann Arbor, MI, pp. 1-143.
Gendelman, H.E., et al., "Evaluation of the safety and immunomodulatory effects of sargramostim in a randomized, double-blind phase 1 clinical Parkinson's disease trial" NPJ Parkinson's Disease (2017) 3:10.
Brodacki, B., et al., "Serum interleukin (IL-2, IL-10, IL-6, IL-4), TNFa and INFg concentrations are elevated in patients with atypical and idiopathic parkinsonism" Neuroscience Letters (2008) 441:158-162.
Mbongue, J.C., et al., "The Role of Indoleamine 2, 3-Dioxygenase in Immune Suppression and Autoimmunity" Vaccines (2015) 3:703-729.
Hill, M., et al., "IDO expands human CD4+CD25high regulatory T cells by promoting maturation of LPS-treated dendritic cells" Eur. J Immunol. (2007) 37:3054-3062.
Kwidzinski, E., et al., "IDO expression in the brain: a double-edged sword" J. Mol. Med. (2007) 85:1351-1359.
Heyes, M.P., et al., "Different kynurenine pathway enzymes limit quinolinic acid formation by various human cell types" Biochem. J. (1997) 326:351-356.

\* cited by examiner

*Primary Examiner* — Daniel E Kolker
*Assistant Examiner* — Aditi Dutt
(74) *Attorney, Agent, or Firm* — Robert C. Netter, Jr.; Dann, Dorfman, Herrell & Skillman

(57) ABSTRACT

The present invention provides novel biomarkers for regulatory T cells (Treg) function and Parkinson's disease.

4 Claims, 11 Drawing Sheets

BIOMARKERS FOR MONITORING IMMUNE TRANSFORMATION

Figure 1:
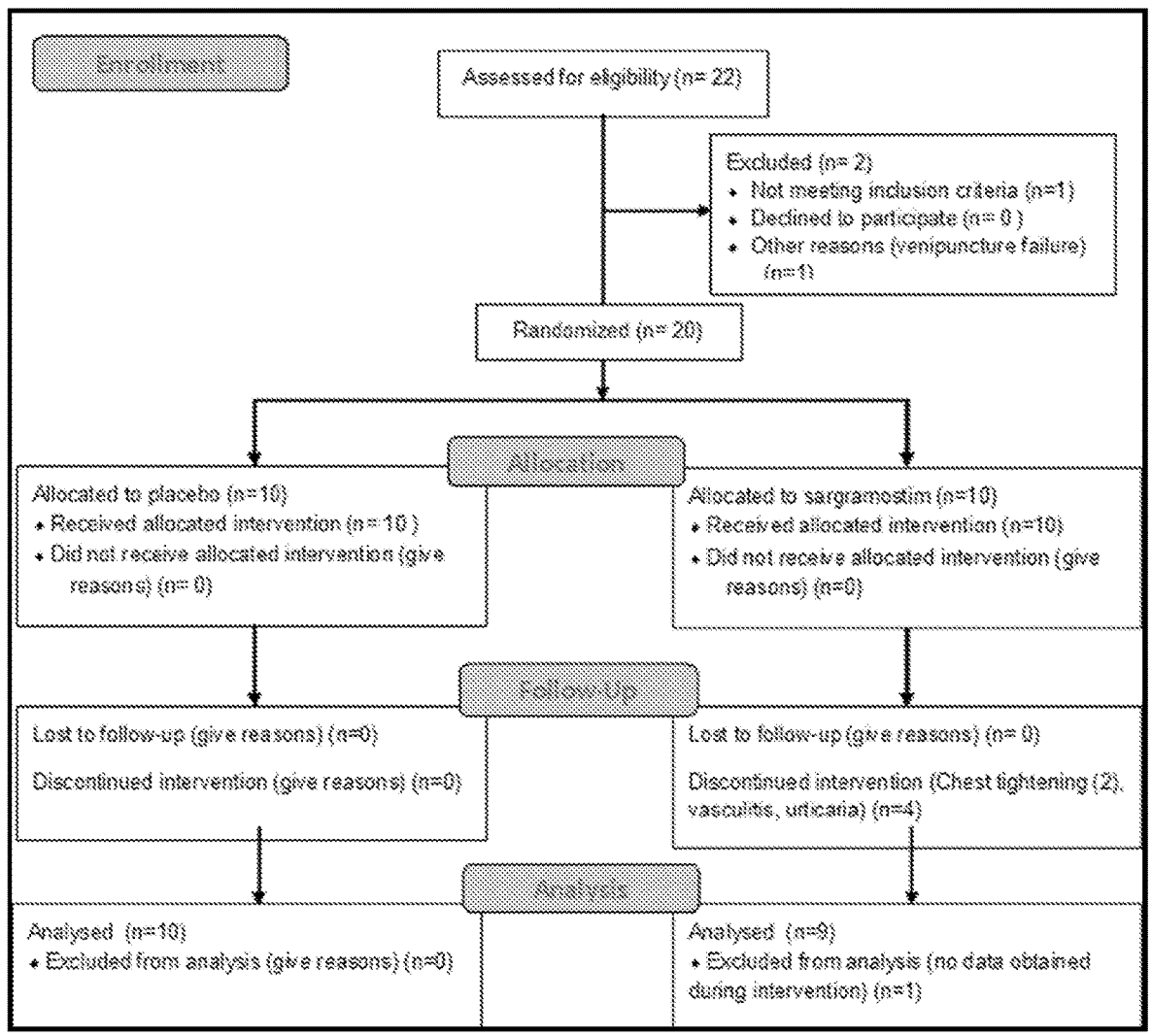

This application is a 0371 application of PCT/US2017/029111, filed Apr. 24, 2017, which claims priority under 35 U.S.C. §119 (e) to U.S. Provisional Patent Application No. 62/326,062, filed Apr. 22, 2016. The foregoing applications are incorporated by reference herein.

This invention was made with government support under Grant Nos. R01-NS034139; R01-NS070190; and R01-NS034239 awarded by the National Institutes of Health and Grant No. W81XWH11-1-0700 awarded by the Department of Defense. The government has certain rights in the invention.

FIELD OF THE INVENTION

The present invention relates generally to Parkinson's disease. More specifically, the present invention relates to biomarkers for Parkinson's disease.

BACKGROUND OF THE INVENTION

Parkinson's disease (PD), the most common neurodegenerative movement disorder, is a progressive and debilitating disease that affects up to five million people worldwide and may double by 2050 (Olanow et al. (2009) Neurology 72 (Suppl 4):S1-S136; Ahlskog, J. E. (2011) Mayo Clin. Proc., 86:1211-6; Schapira, A. H. (2009) Trends Pharmacol. Sci., 30:41-7). Characteristic movement deficits parallel reductions in striatal dopamine and progressive loss of substantia nigra pars compacta neurons and their striatal connections. Lewy bodies containing aggregated and nitrated α-synuclein (N-α-syn) released into the extraneuronal environment induce activated microglia and affect the emergence of effector T cell (Teff) populations. Brain-infiltrating macrophages and microglia produce pro-inflammatory neurotoxins that damage surrounding neurons and are exacerbated by peripheral N-α-syn-induced Teff (Benner et al. (2008) PLoS One 3(1):e1376; Hirsch et al. (2003) J. Neural. Transm. Suppl., 65:89-100). In contrast, regulatory T cells (Treg) maintain immunological tolerance and attenuate inflammation (Sakaguchi, S. (2004) Annu. Rev. Immunol., 22:531-62; Coombes et al. (2005) Immunol. Rev., 204:184-94). Moreover, neurodestructive Th1 and Th17 cells can be transformed into neuroprotective Treg (Reynolds et al. (2010) J. Immunol., 184(5):2261-71).

Despite knowledge of disease mechanisms, therapeutic modalities remain ineffective. Current PD treatments fail to suppress neurodegeneration or halt or reverse disease progression (Suchowersky et al. (2006) Neurology 66:976-82). Therapies aimed at halting the root cause of neurodegeneration are sorely needed. Indeed, current PD therapies are principally symptomatic and focus on restoration of dopaminergic neuronal function (Ahlskog, J. E. (2011) Mayo Clin. Proc., 86:1211-6). Dopamine levels are increased by the use of levodopa and carbidopa (to inhibit peripheral metabolism of levodopa). Dopamine agonists, such as pramipexole and ropinirole, activate dopaminergic neurons to dopamine (Ahlskog, J. E. (2011) Mayo Clin. Proc., 86:1211-6). Monoamine oxidase (MAO-B) inhibitors, selegiline, and rasagiline reduce dopamine breakdown (Schapira, A. H. (2009) Trends Pharmacol. Sci., 30:41-7). These can manage motor symptoms but do not halt disease progression. When patients become refractory to these medicines, subthalamic nucleus deep brain stimulation (STN DBS) is one of few alternatives (Rascol et al. (2011) Mov. Disord., 26:1072-82; Ahlskog, J. E. (2007) Neurology 69:1701-11; Welter et al. (2002) Brain 125:575-83). Other debilitating symptoms include sleep disorders, hypotension, bladder dysfunction, erectile dysfunction, constipation, pain, depression, and cognitive impairment with psychosis, visual hallucinations, and dementia (Ahlskog, J. E. (2007) Neurology 69:1701-11; Chaudhuri et al. (2006) Lancet Neurol., 5:235-45; Langston, J. W. (2006) Ann. Neurol., 59:591-6). Current treatment regimens are palliative, targeting only symptoms and frequently become refractory, while no curative or interdictive treatment exists. Thus, new approaches to managing PD must look beyond the dopaminergic nigrostriatal system (Ahlskog, J. E. (2007) Neurology 69:1701-11; Langston, J. W. (2006) Ann. Neurol., 59:591-6; Obeso et al. (2010) Nat. Med., 16:653-61).

SUMMARY OF THE INVENTION

In accordance with the instant invention, methods for determining the efficacy of a neurodegenerative disease treatment are provided. The methods can be performed in vitro or in vivo. In a particular embodiment, the method comprises administering the neurodegenerative disease treatment to a subject having the neurodegenerative disease and measuring the amount of at least one metabolite of the tryptophan pathway in a biological sample obtained from the subject. In a particular embodiment, the method comprises delivering the neurodegenerative disease treatment to a sample comprising T cells and measuring the amount of at least one metabolite of the tryptophan pathway in the sample. The measured metabolites of the tryptophan pathway may comprise one, two, or all three of L-kynurenine, quinolinic acid, and serotonin. An increase in the amount of L-kynurenine or quinolinic acid after administration of the neurodegenerative disease treatment indicates the neurodegenerative disease treatment is effective against the neurodegenerative disease. A decrease in the amount of serotonin after administration of the neurodegenerative disease treatment indicates the neurodegenerative disease treatment is effective against the neurodegenerative disease. In a particular embodiment, neurodegenerative disease is Parkinson's disease. In a particular embodiment, the biological sample is blood or serum. In a particular embodiment, the neurodegenerative disease treatment is a therapy or a drug treatment such as the administration of an immune modulator, granulocyte macrophage-colony stimulating factor (GM-CSF) (such as sargramostim), GM-CSF analogs or derivatives, vasoactive intestinal peptide receptor 2 (VIPR2, also known as VPAC2) agonists (e.g., LBT-3627), vasoactive intestinal peptide (VIP), VIP analogs or derivatives, therapeutics causing upregulation of GM-CSF in a patient including but not limited to gene therapies, vaccines, or cell therapies.

In accordance with another aspect of the instant invention, methods of monitoring or measuring regulatory T cells (Treg) function or activity are provided. In a particular embodiment, the method comprises measuring the amount of at least one metabolite of the tryptophan pathway in a sample at different timepoints. In a particular embodiment, methods of determining whether a compound modulates regulatory T cells (Treg) function or activity are provided. The methods can be performed in vitro or in vivo. In a particular embodiment, the method comprises contacting a sample comprising T cells with the compound and measuring the amount of at least one metabolite of the tryptophan pathway in the sample. In a particular embodiment, the method comprises administering the compound or therapy to a subject and measuring the amount of at least one metabolite of the tryptophan pathway in a biological sample obtained from the subject. The measured metabolites of the tryptophan pathway may comprise one, two, or all three of L-kynurenine, quinolinic acid, and serotonin. An increase in the amount of L-kynurenine or quinolinic acid indicates the compound increases Treg function or activity. A decrease in the amount of serotonin indicates the compound increases Treg function or activity. In a particular embodiment, the subject has a neurodegenerative disease such as Parkinson's disease. In a particular embodiment, the biological sample is blood or serum. In a particular embodiment, the compound is an immune modulator, granulocyte macrophage-colony stimulating factor (GM-CSF) (such as sargramostim), GM-CSF analogs or derivatives, vasoactive intestinal peptide receptor 2 (VIPR2, also known as VPAC2) agonists (e.g., LBT-3627), vasoactive intestinal peptide (VIP), VIP analogs or derivatives, therapeutics causing upregulation of GM-CSF in a patient including but not limited to gene therapies, vaccines, or cell therapies. In a particular embodiment, the increase in Treg function or activity comprises an increase in the number of Treg cells.

In accordance with another aspect of the instant invention, methods of treating, inhibiting, or preventing a neurodegenerative disease such as Parkinson's disease in a subject are provide. In a particular embodiment, the method comprises administering sargramostim to the subject.

BRIEF DESCRIPTIONS OF THE DRAWING

FIG. 1 provides a flow diagram of patient recruitment and treatment. Twenty-two PD patients were initially recruited to participate in an intention-to-treat trial. One patient failed to meet inclusion criteria and another was excluded due to inability to provide blood by venipuncture. Twenty patients were randomized, and 10 patients were allocated to receive sargramostim and 10 to receive placebo. In the sargramostim-treated group, 2 withdrew due to chest-tightness or bone pain, 1 withdrew due to leukoclastic vasculitis, and 1 withdrew due to a urticarial response. For one patient that withdrew due to feelings of chest-tightness, no data was obtained during intervention, but pre-treatment data was analyzed. All patients allocated to placebo were available for analysis.

Figure 2:
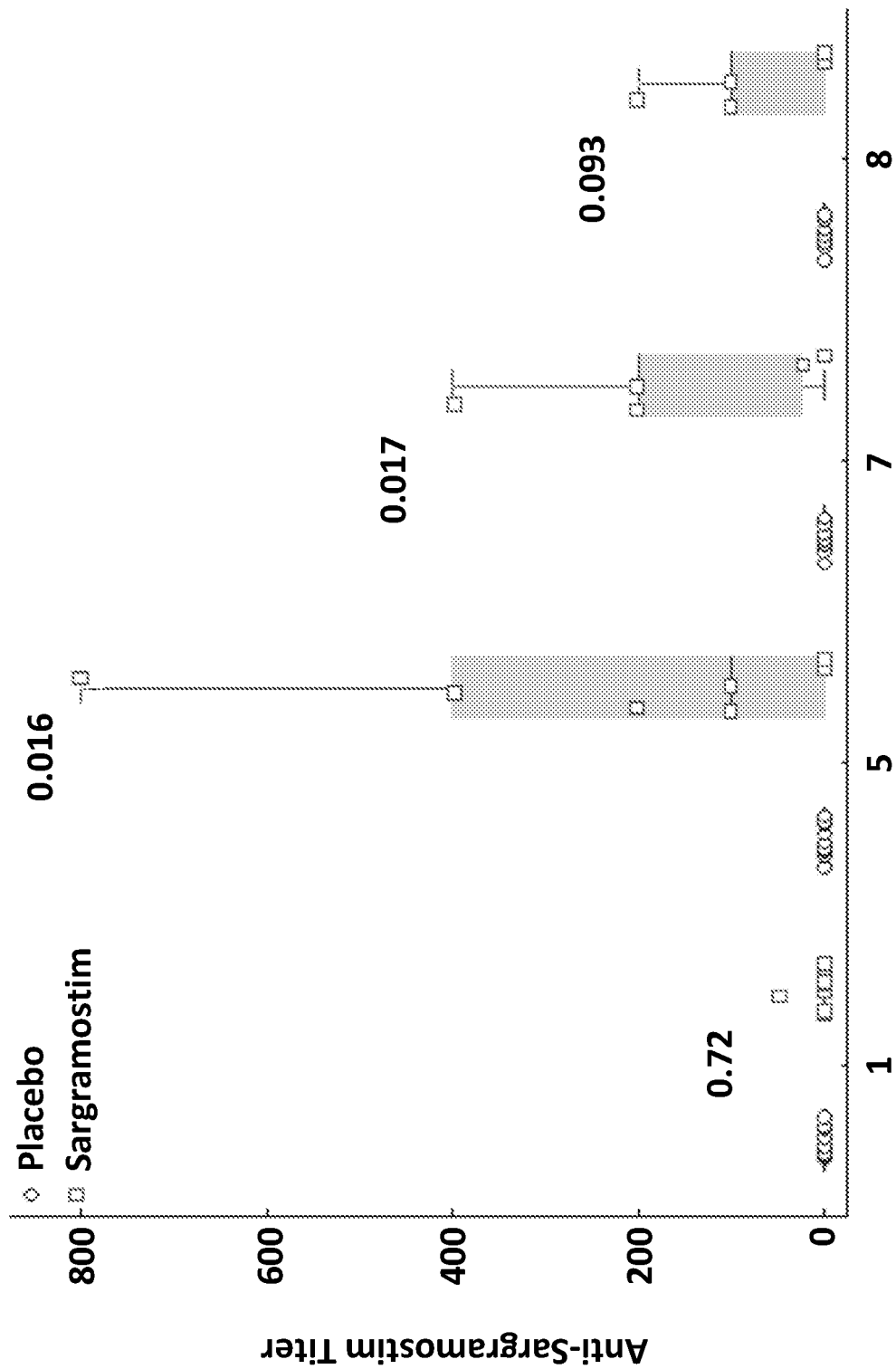

FIG. 2 shows anti-sargramostim antibodies in serum of treated PD patients. Serum samples from PD patients treated with placebo (open circles) or sargramostim (open boxes) were obtained at weeks −8, 4, 8, and 12 relative to initiation of treatment (visits 1, 5, 7, and 8). Samples were initially screened by sargramostim-specific ELISA. Positive samples were confirmed by immunoprecipitation assay; ELISA endpoint titers defined as the reciprocal of the last dilution above the titration; and antibody neutralization using a CSF2R-expressing cell-based assay system with a luciferase reporter detecting functional sargramostim. Medians (line), IQRs (box), and non-outlier ranges (whiskers) were determined for ELISA titers of anti-sargramostim antibodies for PD patients treated with placebo ($n_{v1}=8$, $n_{v5}=9$, $n_{v7}=7$, and $n_{v8}=8$) or sargramostim ($n_{v1}=8$, $n_{v5}=7$, $n_{v7}=5$, and $n_{v8}=5$). Pairwise comparisons of anti-sargramostim titer medians between placebo- and sargramostim-treated patients for each visit were determined by Mann-Whitney U test and p values provided for each visit.

Figure 3A:
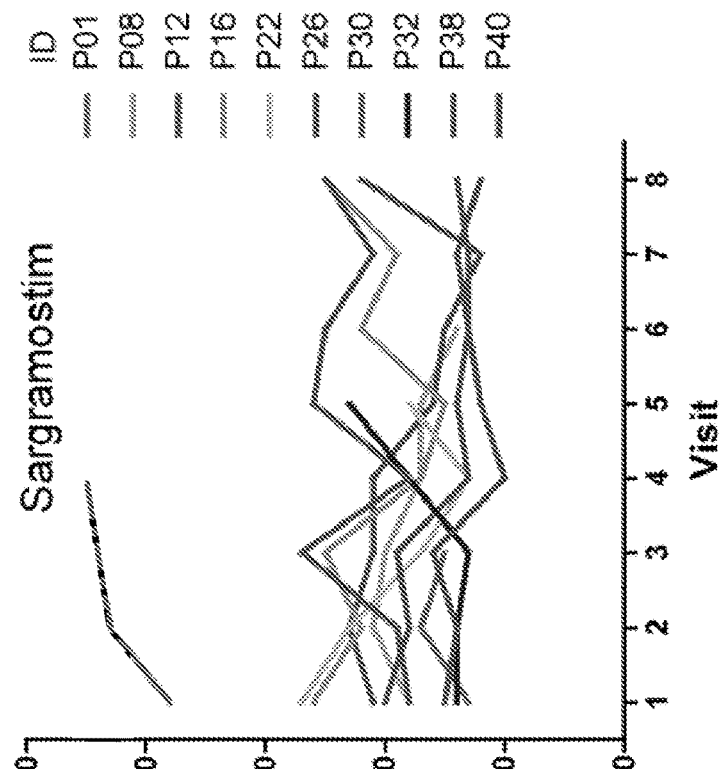
Figure 3A:
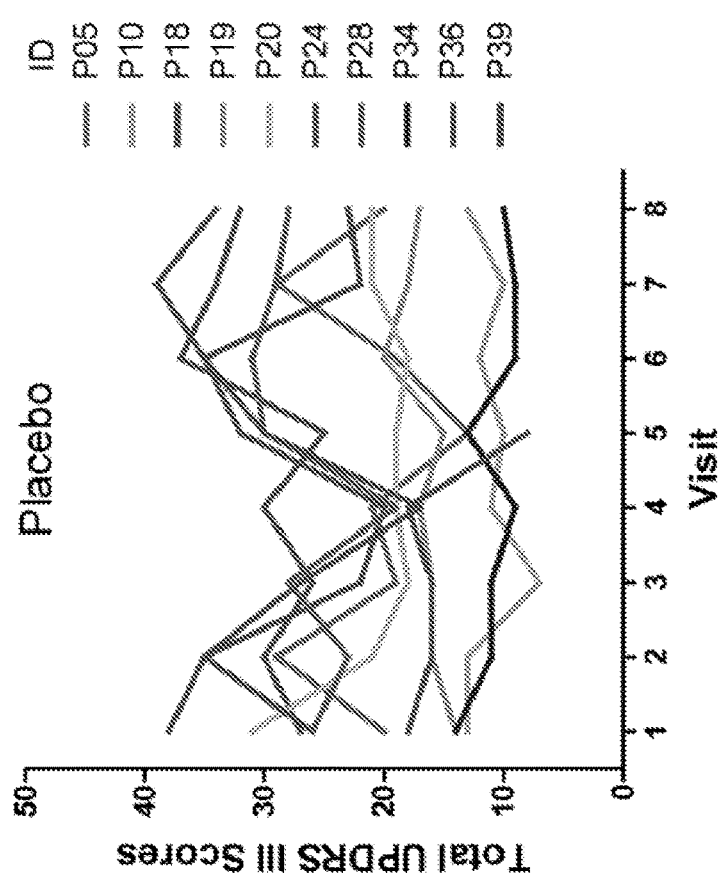
Figure 3B:
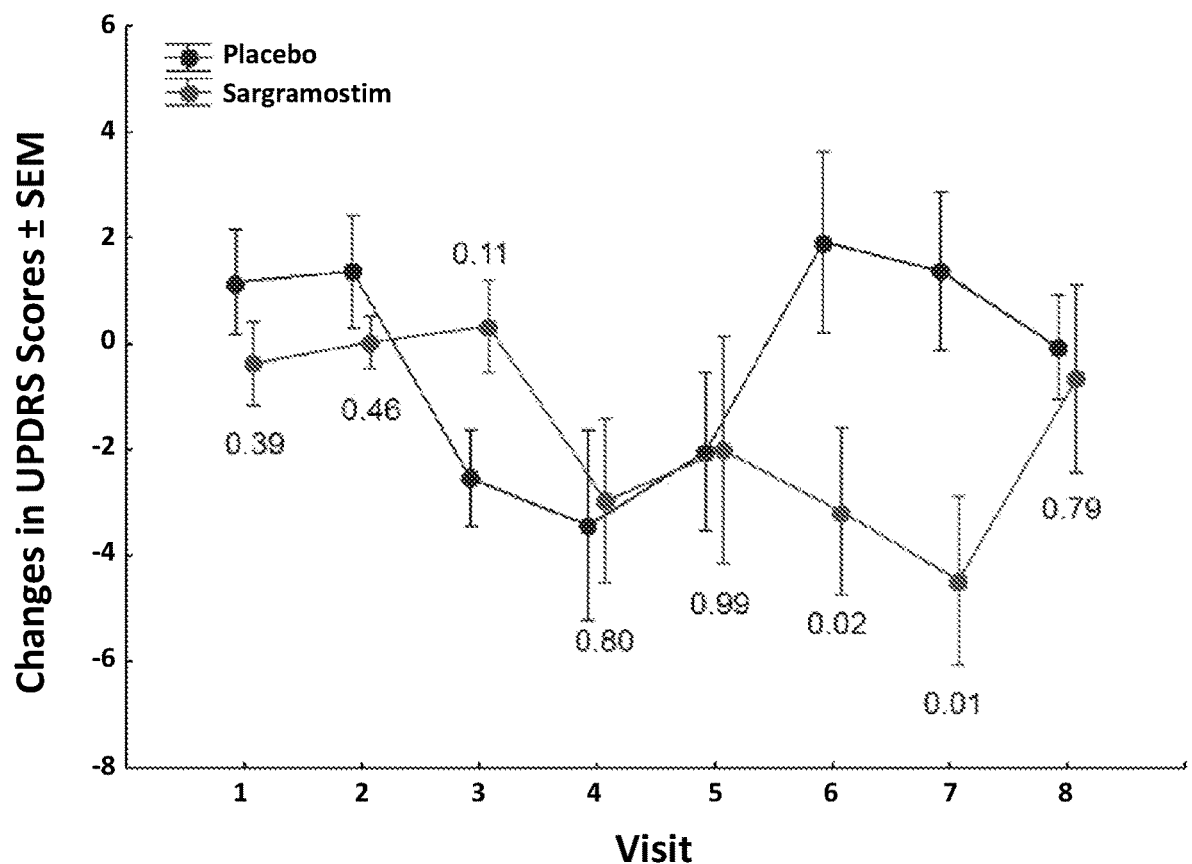
Figure 3C:
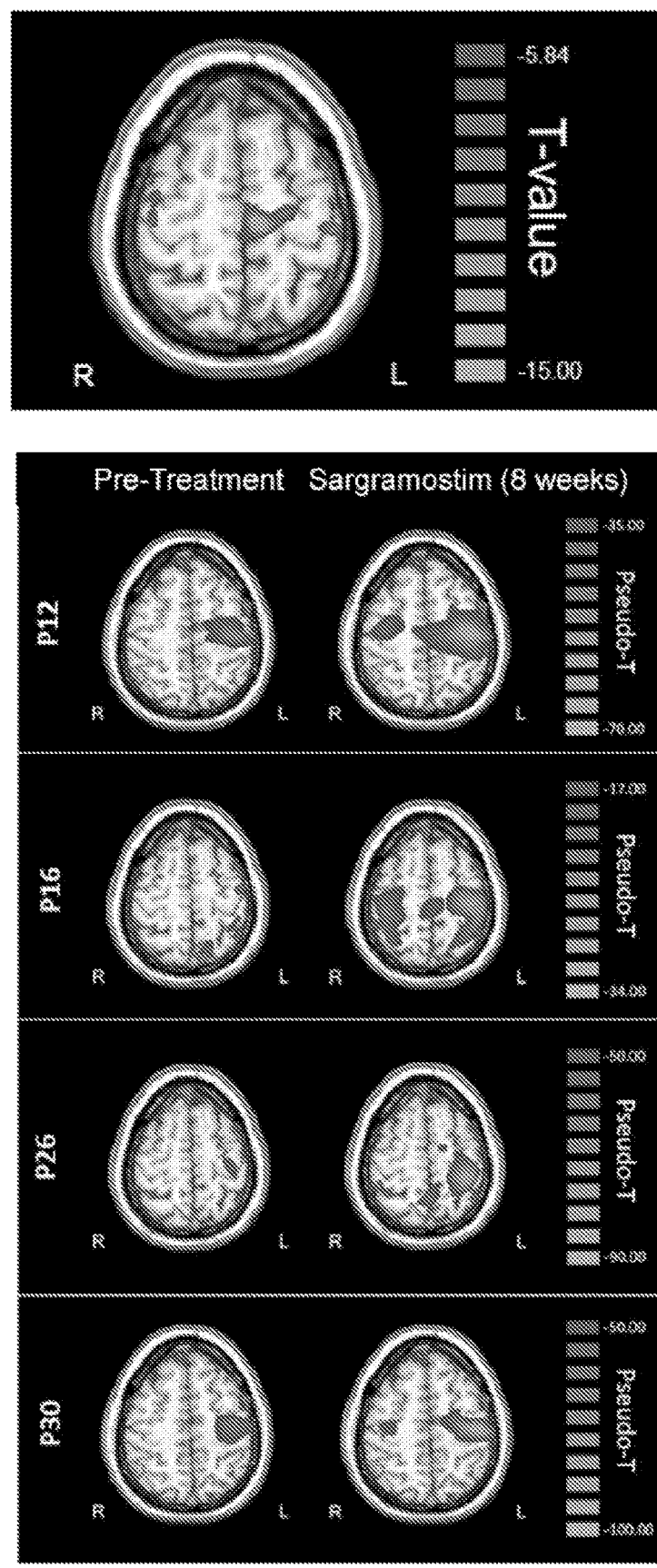
Figure 4A:
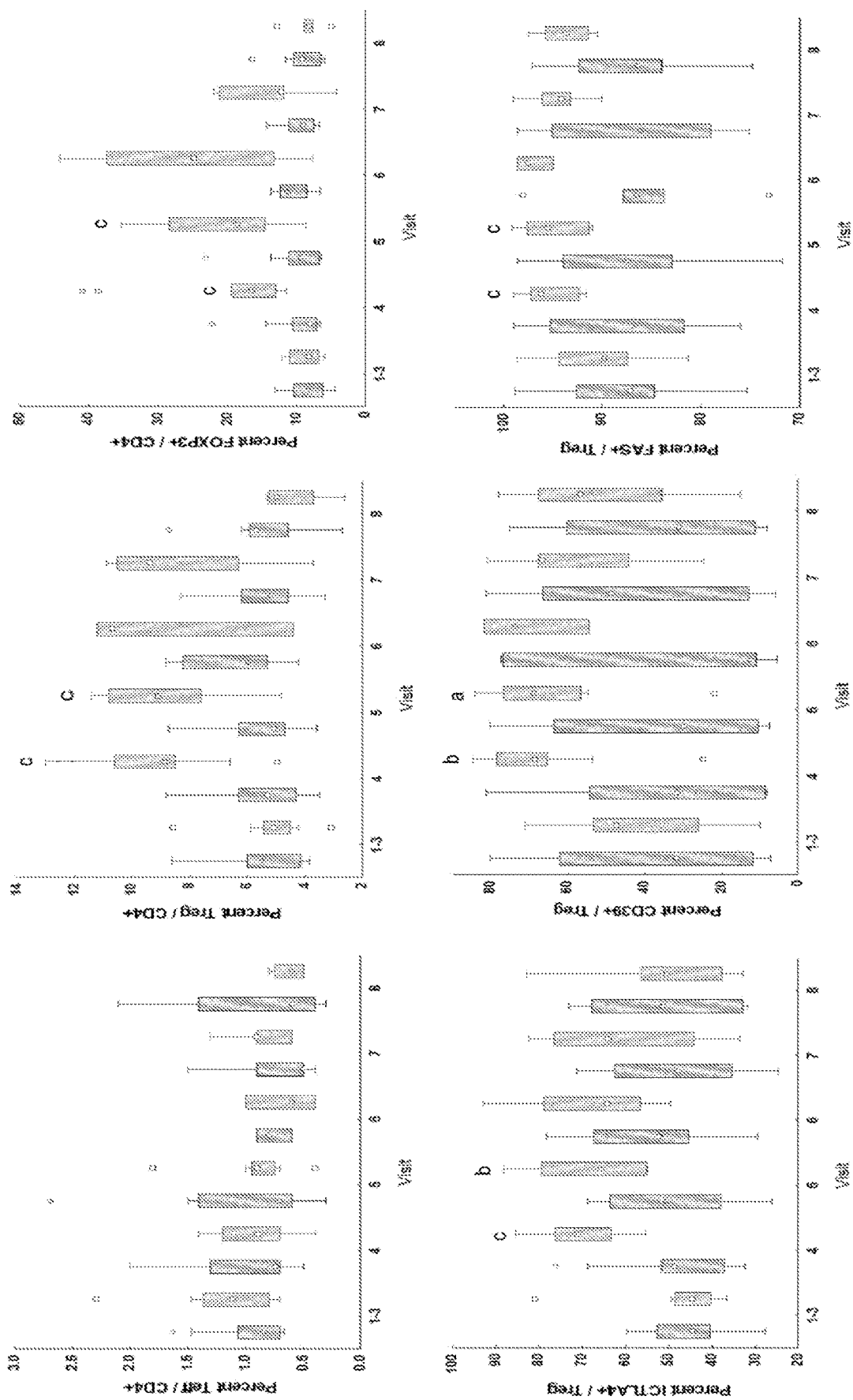
Figure 4B:
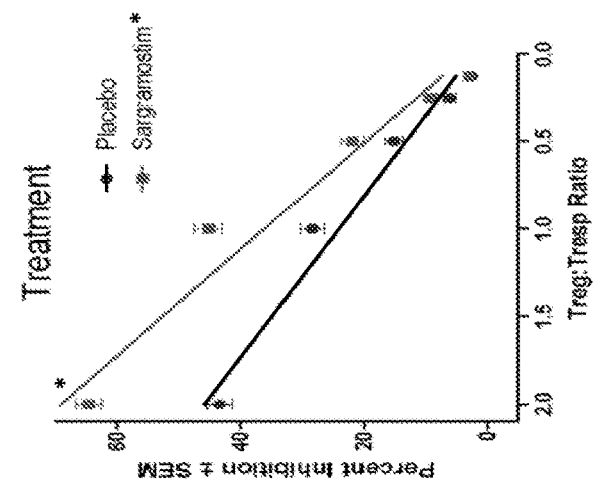
Figure 4B:
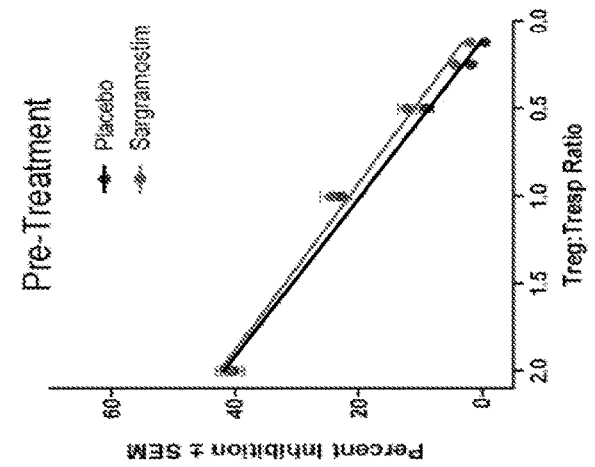
Figure 4B:
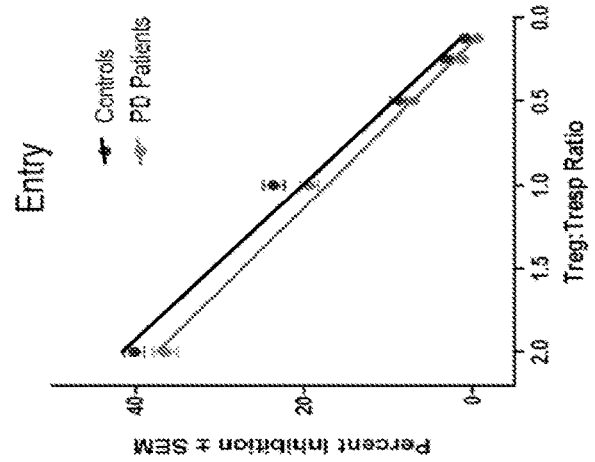

FIGS. 3A-3C show the neurophysiological assessment by Unified PD Rating Scale Part III (UPDRS III) and magnetoencephalography (MEG) evaluations. PD patients were randomized to receive placebo or sargramostim. FIG. 3A: UPDRS, part III scores of each individual patient were assessed at 0, 4, and 8 weeks (visits 1-3) before treatment (Pre-Treatment); at 2, 4, 6, and 8 weeks (visits 4-7) during treatment (Placebo or Sargramostim); and at 4 weeks (visit 8) after cessation (Placebo or Sargramostim Post-Treatment). Higher scores represent more severe motor symptoms. FIG. 3B: Changes from baseline UPDRS III scores were determined at each visit for placebo- and sargramostim-treated patients using the mean scores of visits 1-3 for each patient as baseline from which to normalize. Changes in scores from each randomized treatment group were normally distributed and did not violate Levene's test for homoscedasticity ($p>0.05$). Factorial ANOVA showed an effect of randomized treatment group ($p=0.05$) and marginal effects of visit ($p=0.07$) and treatment-by-time ($p=0.05$). Fisher's least significant difference (LSD) post-hoc tests were used to determine pairwise differences between placebo and sargramostim treatment at each visit. FIG. 3C: MEG assessment of beta ERD in PD patients. Paired sample t-test comparison of beta ERD activity at baseline (pre-treatment) and during treatment for the group of PD patients receiving sargramostim. Significant increases in beta ERD amplitudes are noted in the left and right precentral gyri, right premotor cortex, and supplementary motor area (SMA) (top panel). Increases in beta ERD activity from pre- to sargramostim-treatment are shown for individual patients. Compared to pre-treatment, the left precentral gyms showed a significant effect of visit [$F(2,9)=8.869$, $p=0.007$] and visit-by-group interaction [$F(2,9)=6.04$, $p=0.022$], which was quadratic [$F(1,10)=10.772$, $p=0.008$]. The right precentral gyms also showed a visit-by-group interaction [$F(2,9)=3.321$, $p=0.06$], which also was quadratic [$F(1,10)=5.447$, $p=0.04$]. The right premotor cortex showed a marginal effect of visit [$F(2,9)=3.050$, $p=0.07$] and the effect was quadratic [$F(1,10)=6.124$, $p=0.03$]. Quadratic interactions were explained as beta ERD amplitudes that increase from pretreatment baseline while on sargramostim and return to baseline levels after termination of treatment. Patients treated with placebo ($n=6$) showed no significant effects on ERD activity FIGS. 4A-4B show that sargramostim increases Treg frequency and function. Peripheral blood lymphocytes from PD patients treated with placebo or sargramostim were assessed for the expression of Treg phenotype and function. FIG. 4A: Flow cytometric analyses of CD4+ Teffs (CD4+ CD127hiCD25hi) or Tregs (CD4+CD12loCD25hi) over a 3-month mean baseline (visits 1-3), every 2 weeks after the initiation of treatment (visits 4-7), and 4 weeks after discontinuation of treatment (visit 8). Plots represent the medians, IQRs (boxes), and non-outlier ranges (whiskers) of T cells from PD patients treated with placebo or sargramostim. Levels of T cell subsets from PD patients treated with placebo ($n=6$-$10$) or sargramostim ($n=5$-$9$) were compared by Mann-Whitney U test with p-values$<0.10^a$, $0.05^b$, or $0.01^c$. Analyses of visit 6 biomarkers were included in the latter half of the study. FIG. 4B: Enriched Treg isolates were assessed for their capacities to suppress CD3/CD28-stimulated Tresp from a healthy donor. Tregs were serially-diluted two-fold and co-stimulated with a constant number of CFSE-stained Tresps to yield decreasing Treg:Tresp ratios. Baseline Treg activity as percentage inhibition of proliferation was determined for non-parkinsonisn controls ($n=17$) and non-allocated PD patients ($n=20$) at 8, 4, and 0 weeks before treatment initiation (Entry, visits 1-3); for randomized PD patients prior to initiation of treatment (Pre-Treatment, visits 1-3); and at 2, 4, 6, and 8 weeks after initiation (Treatment, visits 4-7). Comparison of differences in slope or elevation as an indicator of Treg activity was determined by linear regression analyses for baseline paired controls and PD patients ($p_{slope}$=0.49, $p_{devation}$=0.065, n=17) (Entry); for baseline of placebo (n=10) or sargramostim (n=10) randomized PD patients ($p_{stope}$=0.59, $p_{devation}$=0.17) (Pre-Treatment); and for PD patients during treatment with sargramostim (n=5-9) compared to placebo (n=9-10) ($p_{slope}$=0.063, $p_{elevation}$=0.058) (Treatment). Comparison of Treg activity from pre-treated and treated patients randomized to sargramostim group ($p_{slope}$=0.039) or placebo group ($p_{slope}$=0.88, $p_{elevation}$=0.04).

Figure 5A:
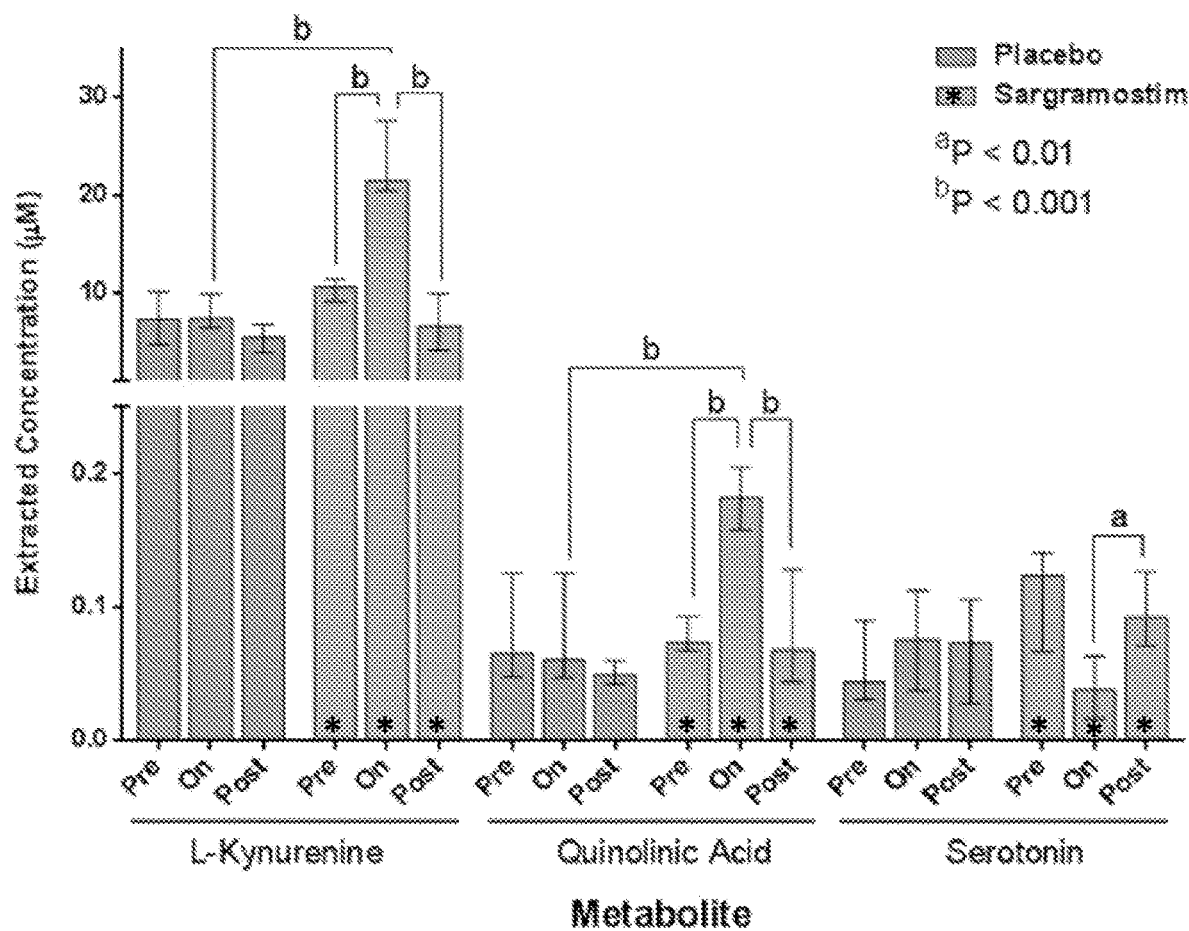
Figure 5B:
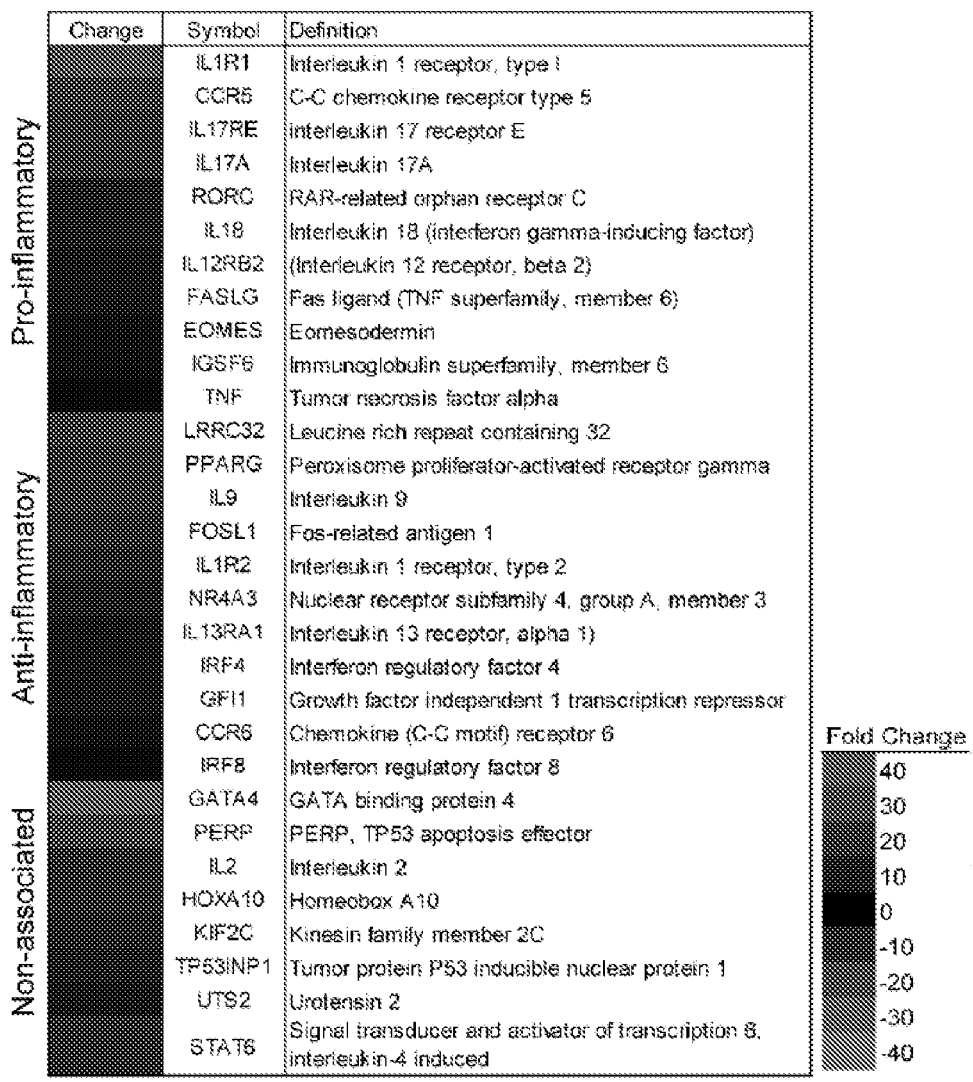
Figure 5C:
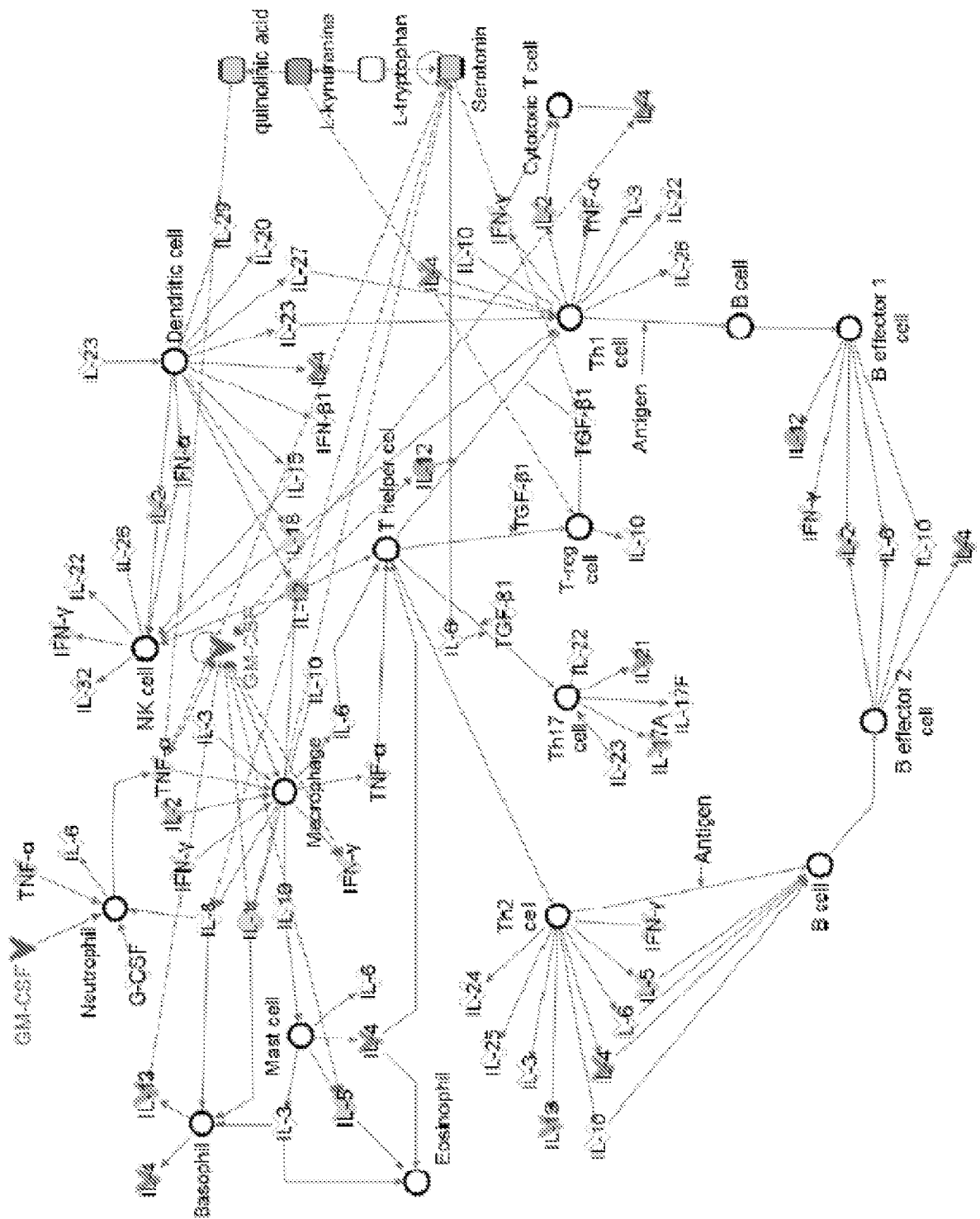
Figure 5D:
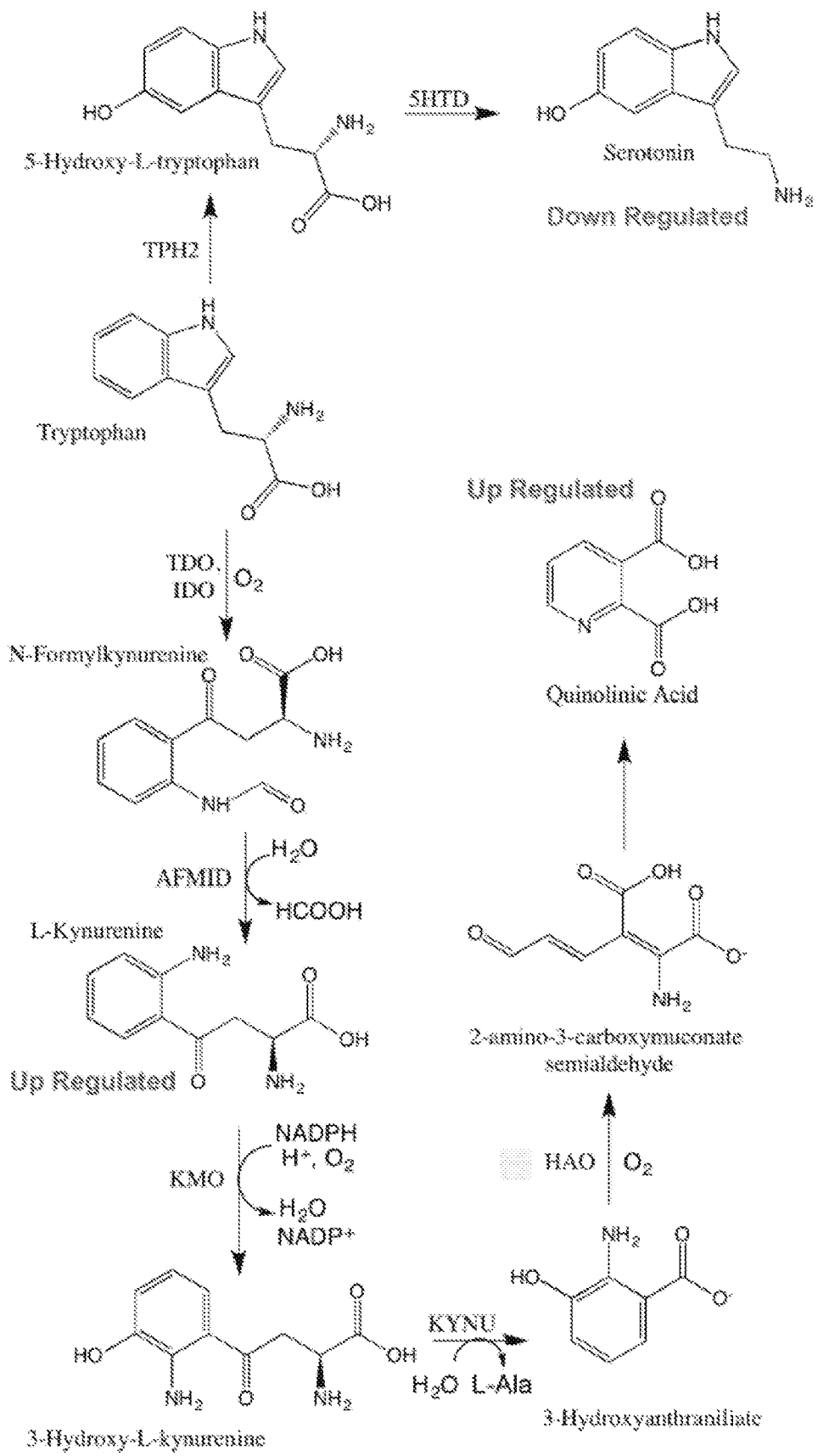

FIGS. 5A-5D show that sargramostim induces changes in pro- and anti-inflammatory mediators in serum and genes in T cells from PD patients. FIG. 5A: Metabolomic analyses of serum from PD patients prior to treatment (Pre, visits 1 and 2), at weeks 4 and 8 during treatment (On, visits 5 and 7), and at 4 weeks after treatment cessation (Post, visit 8). When available, results from the same patient, but at different visits were averaged and binned into pre- or on-treatment. Medians and IQRs of tryptophan metabolite concentrations were determined from patients randomized into placebo group ($n_{Pre}$=8, $n_{On}$=9, $n_{Post}$=8) or sargramostim group ($n_{Pre}$=9, $n_{On}$=7, $n_{Post}$=5). Comparison of median metabolite concentrations between pre-, on-, and post-treatment samples and between samples from placebo and sargramostim treated groups were determined by Mann-Whitney U tests. Of the 18 targeted metabolites from the tryptophan pathway, many were below the calibration curve or detection limits, or were unchanged. Concentrations of kynurenine and quinolinic acid were found to be up-regulated; whereas serotonin was down-regulated. Tryptophan concentrations were not significantly changed regardless of treatment or visit. FIG. 5B: Significant increase or decrease in expression of genes by CD4+CD25− T cells from PD patients treated with sargramostim compared to placebo. Genes are divided into those associated with Th1 and Th17 cells (Pro-inflammatory), Th2 and Tregs (Anti-inflammatory) and general T cell proliferation and differentiation (Non-associated). Significant differences are indicated by a heat map. The map ranged from 40-fold increase to 40-fold decrease. FIG. 5C: Ingenuity Pathway analyses performed on up- or down-regulated genes to identify putative network associations involved in hematological development and T cell function. Genes and mediators that are up-regulated are shaded with the darker shades indicating more up-regulation; and nodes in white represent putative associated function. FIG. 5D: Enzymes in tryptophan pathway include TPH2, tryptophan hydroxylase-2; SHTD, 5-hydroxytryptophan decarboxylase; TDO, tryptophan 2,3-dioxygenase; IDO, indolamine 2,3-dioxygenase; AFMID, arylformamidase; KMO, kynurenine 3-monooxygenase; KYNU, kynureninase; and HAO, 3-hydroxyanthranilate 3,4-dioxygenase.

DETAILED DESCRIPTION OF THE INVENTION

The proteinaceous aggregates in Lewy bodies (LB) comprised mostly of nitrated and aggregated α-synuclein (α-syn) can break immunological tolerance and induce Teff (specifically Th17)-mediated neurodestructive activities (Spillantini et al. (1998) Proc. Natl. Acad. Sci., 95: 6469-73; Spillantini et al. (1997) Nature 388:839-40; Benner et al. (2008) PLoS One 3:e1376). LBs are present in areas of neurodegeneration and reactive microglia accumulation. These include areas of the central, peripheral, and enteric nervous systems (Langston, J. W. (2006) Ann. Neurol 59: 591-6; Braak et al. (2008) Neurology 70:1916-25; Braak et al. (2002) J. Neurol., 249 (Suppl 3): III/1-5; Braak et al. (2003) Neurobiol. Aging 24:197-211). In the PD brain, such progressive degeneration amongst the dopaminergic neurons results in reduced dopamine neurotransmission and loss of neural control in motor function. This is characterized by the clinical features of PD that include, but are not limited to resting tremor, bradykinesia, rigidity, and gait dysfunctions (Dauer et al. (2003) Neuron 39:889-909).

Associations between microglial activation and adaptive immune activities in the pathobiology of PD are known (Hirsch et al. (2009) Lancet Neurol., 8:382-97; Appel et al. (2010) Trends Immunol., 31:7-17). In PD, extraneuronal nitrated alpha synuclein (N-α-syn) induces sustained local microglial inflammatory responses, which in turn induces subsequent encephalopathies and trafficking of N-α-syn to the peripheral lymphoid tissues, wherein neurodestructive Teff are generated (McGeer et al. (2008) Mov. Disord., 23:474-83; Giasson et al. (2000) Science 290:985-9). N-α-syn elicits significant neurotoxic immune responses characterized by induction of inflammatory neurodestructive Th17 CD4+ T cells. In contrast, Treg can transform this neurodestructive Th17 Teff response to robust neuroprotection as measured by dopaminergic neuronal survival in the nigrostriatum (Reynolds et al. (2010) J. Immunol., 184: 2261-71). The induction of Treg immune response has been shown to protect against nigrostriatal neurodegeneration in rodent PD models (Kosloski et al. (2013) J. Neuroimmunol., 265(1-2): 1-10; Mangano et al. (2011) Neurobiol. Dis., 43(1):99-112). While this is a unique disease-specific survival function, Treg are indeed known to maintain immunological tolerance to self as well as tissue homeostasis and prevent autoimmunity by attenuating inflammation elicited by infection or tissue injuries (Sakaguchi et al. (1995) J. Immunol., 155: 1151-64; Sakaguchi et al. (2003) Novartis Foundation Symposium 252:6-16; Sakaguchi, S. (2004) Ann. Rev. Immunol., 22:531-62; Kim et al. (2007) Nature Immunol., 8: 191-7; Coombes et al. (2005) Immunol. Rev., 204:184-94; Bourreau et al. (2009) Inf. Immun., 77:1465-74; Cederbom et al. (2000) Eur. J. Immunol., 30:1538-43; Kipnis et al. (2002) Proc. Natl. Acad. Sci., 99:15620-5). Thus, the induction of Treg responses control neuroinflammatory responses that precede subsequent neurodegenerative processes and would be of therapeutic benefit in preventing PD-associated neurodegeneration.

Further, the peripheral blood of PD patients show levels of decreased naïve (CD4+CD45RA+) T cells and increased memory (CD4+CD45RO+) T cells; increased activated CD4+ T cells expressing FAS, a cell death receptor found on activated cells; increased interferon gamma (IFN-γ)-producing Th1 cells; decreased IL-4-producing Th2 cells; and decreased CD4+CD25+ T cell levels (Fiszer et al. (1994) Acta Neurologica Scandinavica 90:160-6; Hisanaga et al. (2001) Arch. Neurol., 58: 1580-3; Baba et al. (2005) Parkinsonism Relat. Disord. 11:493-8). In PD patients compared to age- and environment-matched caregiver controls, there is a significant reduction in lymphocyte frequency and number (p=0.04) with an overall decrease in CD4+ T cell numbers (p=0.01), as well as a diminished ability of PD Treg to suppress T cell proliferation (Saunders et al. (2012) J. Neuroimmune Pharmacol., 7: 927-38). Importantly, PD patients presented increased frequencies of CD45RO+ CD45RA− memory phenotype CD4+ T cells (Tem) (p=0.03) with increased FAS expression (p=0.03), indicating persistent immune activation. Frequencies of CD4+CD31+ (PE-CAM-1, a cellular adhesion molecule) were decreased in PD (p=0.03). The diminution of these cells and increased frequency of FAS+ T cells can affect apoptosis and contribute to lymphopenia. Moreover, these immune aberrations were associated with progressive motor dysfunction. Changes in CD4+ T cells, Treg and Teff phenotypes were associated with increased disease severity as scored by UPDRS part III evaluation, the most common clinical assessment of disease severity. Compared to caregivers, advanced PD patients have increased CD45RO+ and FAS+ CD4+ T cells and decreased α4β7+ and CD31+CD4+ T cells. The predominance of Tem in more severe stages of disease and the associations in mouse models of PD, wherein N-α-syn specific Teff exacerbate neurodegeneration further support a role of chronic immune activation in disease progression. Thus, chronic immune dysregulation drives PD progression (McGeer et al. (2008) Movement Disorders 23:474-83; Fiszer, U. (2001) Biodrugs: Clin. Immunother., Biopharm. Gene Ther., 15:351-5; Kosloski et al. (2010) J. Neurochem., 114:1261-76).

Herein, restoration of dysregulated Treg responses and attenuation of chronic immune activation in PD has been demonstrated by the administration of granulocyte macrophage-colony stimulating factor (GM-CSF). At enrollment, PD patients showed reduced CD39+ Treg numbers and function. Replicate Teff frequencies were decreased. Sargramostim increased neutrophil, monocyte, eosinophil and CD3+ and CD4+ T cell numbers. Tryptophan metabolism was closely linked to the induction of Treg subsets and their anti-proliferative activities. Significant increases in Treg numbers, function, and tryptophan metabolites were coordinate with improved UPDRS III scores and MEG cortical activities.

GM-CSF is a myeloid growth factor that induces proliferation and differentiation of hematopoetic cells. Sargramostim (tradename Leukine®) is a recombinant human GM-CSF. GM-CSF is a potent inducer of T regulatory cells (Treg) (Sheng et al. (2008) Clin. Immunol., 128: 172-80; Sheng et al. (2011) J. Neuroimmunol., 240-241:65-73; Bhattacharya et al. (2011) J. Leukoc. Biol., 89: 235-49; Kared et al. (2008) Blood 112:2575-8). In a clinical trial to test the efficacy of GM-CSF in 81 Crohn's disease patients and 43 placebo control subjects, significantly more patients in the treatment group experienced disease remission compared to the placebo group (Korzenik et al. (2005) N. Engl. J. Med., 352:2193-201). GM-SCF is also effective in ameliorating neurodegeneration in rodent models and affects neurotransmitter levels (Ha et al. (2005) J. Neurosurg. Spine 2:55-61; Mangano et al. (2011) Neurobiol. Dis., 43: 99-112; Bianchi et al. (1997) NeuroReport 8:3587-359).

Magnetoencephalography (MEG) provides a non-invasive method to study brain activity. Previous electrophysiological studies have shown that PD is associated with a slowing of cortical activity, whereby patients exhibit significantly greater alpha frequency activity along with significantly reduced beta-band activity, relative to age- and sex-matched controls (Bosboom et al. (2006) Clin. Neurophysiol., 117:2521-31; Stoffers et al. (2007) Brain 130:1847-60; Bosboom et al. (2009) Clin. Neurophysiol., 120:910-5; Olde Dubbelink et al. (2013) Neurobiol. Aging 34(2):408-18; Berendse et al. (2007) Parkinsonism Relat. Disord. 13 (Suppl 3): S440-5). Generally these studies have relied on measures of peak frequency, which is known to be highly variable across healthy persons and is non-quantitative. Furthermore, previous MEG and EEG (electroencephalography) studies have exclusively used the coarse analytical framework of scalp- and sensor-based analyses, which carry a number of limitations (Bosboom et al. (2006) Clin. Neurophysiol., 117:2521-31; Stoffers et al. (2007) Brain 130: 1847-60; Bosboom et al. (2009) Clin. Neurophysiol., 120: 910-5; Olde Dubbelink et al. (2013) Neurobiol. Aging 34(2):408-18; Berendse et al. (2007) Parkinsonism Relat. Disord. 13 (Suppl 3): S440-5; Bosboom et al. (2009) J. Neural Transm., 116:193-202; Stoffers et al. (2008) Neuroimage 41: 212-22). Herein, source-space volumetric analyses, such as adaptive beam forming, may be used on the MEG data. The MEG data using these analytical techniques have supported the invasive work by indicating strong beta synchronization during rest in PD and milder beta desynchronization during movement preparation compared to age and sex matched controls. Herein, the amplitude of this pathological beta synchronization/desynchronization may be monitored to evaluate improvements in cortical brain function as a secondary endpoint for PD patients treated with GM-CSF. MEG measures of beta synchronization/desynchronization can yield the earliest indication of decreased severity in PD symptomatology and can serve as a quantitative monitoring tool for evaluating the efficacious effects of the intervention.

Progressive degeneration of dopaminergic neurons in the brains of individuals with PD decreases dopamine neurotransmission and results in loss of motor function. This is characterized by PD features that include, but are not limited to, gait dysfunctions, balance disorders, bradykinesia, resting tremor and rigidity (Dauer et al. (2003) Neuron 39:889-909; Vaillancourt et al. (2000) Clin. Neurophys., 111:2046-2056). In PD, gait impairments often include decreased step length and velocity, shuffling, freezing episodes, dyskinesias, and more frequent falls (Katzel et al. (2012) Parkinson's Disease 2012:1-6; O'Sullivan et al. (2007) Physical Rehabilitation, Philadelphia: F.A. Davis Co.; Durstine et al. (2009) ACSM's exercise management for persons with chronic diseases and disabilities, 3rd ed. Champaign, Ill.: Human Kinetics). These gait deficiencies often result in difficulties in gait initiation, changing the gait speed, walking through doorways, and negotiating turns (Fernandez et al. (2013) Gait Posture 38:956-961; Combs et al. (2014) Gait Posture 39:784-788; Cowie et al. (2010) Neuropsychologia 4899:2750-2757; Huxham et al. (2008) Movement Disord. 23(10):1391-1397). The noted motor deficiencies are not limited to the patient's gait. Individuals with Parkinson's disease develop forces at a slower rate and take a longer time to terminate their force production with their hands (Neely et al. (2013) PLoS 8(3):e58403). This impacts an individual's ability to perform fine motor skills such as picking up a glass and using a pen to signing their name. Motor assessments can be used to quantify subject's mobility, postural balance, upper extremity motor control, and resting state tremors.

In accordance with the instant invention, compositions and methods are provided for the detection and/or diagnosis of a neurodegenerative disease (e.g., Parkinson's disease) and/or assessing the effectiveness of a therapy against a neurodegenerative disease (e.g., Parkinson's disease). Examples of neurodegenerative disease include, without limitation, Alzheimer's disease, Parkinson's disease, Lewy Body disease, amyotrophic lateral sclerosis, prion disease, and Huntington's disease. While the instant invention may be used for other neurodegenerative diseases, the invention will generally be described for convenience in terms of Parkinson's disease.

The present invention describes novel biomarkers for Parkinson's diseases. Metabolites from the tryptophan pathway have been identified that correspond to sargramostim (GM-CSF)-mediated inductions of Treg numbers, frequency and function. These metabolites can be used to monitor Treg function and development and be used to gauge therapeutic efficacy in studies using GM-CSF or other immune modulators that are effective for treating Parkinson's disease. Sargramostim-mediated increases in Treg frequency and function indicate the prevalence of conditions conducive for Treg development. Serum from PD patients prior to, during, and after treatment with sargramostim or placebo was assessed by untargeted metabolomics. The findings indicate the involvement of the tryptophan pathway; metabolites from which regulate inflammation as well as immunological tolerance and Treg development and function. Targeted metabolomics for the tryptophan pathway yielded levels of three key metabolites from sargramostim-treated patients that differed significantly from pre- or post-treatment levels and levels from placebo treated patients. L-Kynurenine concentration from the sargramostim group was 2.3- and 3.0-fold higher than those from pre- or placebo-treated patients, respectively. Quinolinic acid concentration was 2.4-fold higher than those from either pre- or placebo-treated patients. Both metabolites returned to control levels by 4 weeks after treatment. In contrast, serotonin levels from sargramostim-treated patients diminished 2.5-fold ($p=0.03$) and 2.2-fold ($p=0.054$) from levels of pre- and placebo-treated patients. These metabolites can be used to monitor the effectiveness of treatment regimens (e.g., sargramostim-based treatment regimens) in Parkinson's disease as well as other neurodegenerative diseases. These metabolites have the potential to be used to monitor the efficacy of other drug candidates and/or therapies (e.g., those capable of transforming an immune profile—specifically enhancing Treg frequency and function). These biomarkers may also be useful for helping identify patients that would respond to certain treatments such as GM-CSF (e.g., molgramostim or sargramostim), GM-CSF analogs or derivatives, vasoactive intestinal peptide receptor 2 (VIPR2, also known as VPAC2) agonists (e.g., LBT-3627), vasoactive intestinal peptide (VIP), VIP analogs or derivatives, therapeutics causing upregulation of GM-CSF in a patient including but not limited to gene therapies, vaccines, or cell therapies.

In accordance with an aspect of the instant invention, methods for detecting and/or monitoring regulatory T cells (Treg) function, activity, frequency (e.g., number), and/or development are provided. In a particular embodiment, the method comprises detecting and/or measuring at least one component (e.g., metabolite) of the tryptophan pathway (see, e.g., FIG. 5D) in a sample, particularly a biological sample (e.g., serum or blood). In a particular embodiment, the method comprises measuring the amount of at least one metabolite selected from the group consisting of L-kynurenine, quinolinic acid, and serotonin. In a particular embodiment, the method comprises measuring the amount of at least two metabolites selected from the group consisting of L-kynurenine, quinolinic acid, and serotonin. In a particular embodiment, the method comprises measuring the amount of L-kynurenine, quinolinic acid, and serotonin. An increase in the amount of L-kynurenine and/or quinolinic acid indicates an increase in regulatory T cells (Treg) function, activity, frequency, and/or development. A decrease in the amount of serotonin indicates an increase in regulatory T cells (Treg) function, activity, frequency, and/or development. In a particular embodiment, the method further comprises detecting and/or measuring the component (e.g., metabolite) of the tryptophan pathway in the same or corresponding sample, particularly a biological sample (e.g., serum or blood), at a different time point (e.g., prior to a therapy or administration of a compound (e.g., drug or drug candidate) to the sample) for comparison. The compound may be any natural or synthetic compound as described hereinbelow (for the neurodegenerative disease treatment).

In a particular embodiment, the method further comprises comparing the amount of the component (e.g., metabolite) of the tryptophan pathway with a standard (e.g., the amount of the component (e.g., metabolite) of the tryptophan pathway detected or measured may be compared to the amount from a corresponding biological sample from an untreated control or).

In accordance with an aspect of the instant invention, methods for determining whether a compound or therapy affects regulatory T cells (Treg) function, activity, frequency (e.g., number), and/or development are provided. In a particular embodiment, the method comprises detecting and/or measuring at least one component (e.g., metabolite) of the tryptophan pathway (see, e.g., FIG. 5D) in a sample, particularly a biological sample (e.g., serum or blood), after delivery of the compound or therapy to a sample comprising T cells (e.g., delivery or administration of the compound or therapy to a subject). In a particular embodiment, the method comprises measuring the amount of at least one metabolite selected from the group consisting of L-kynurenine, quinolinic acid, and serotonin. In a particular embodiment, the method comprises measuring the amount of at least two metabolites selected from the group consisting of L-kynurenine, quinolinic acid, and serotonin. In a particular embodiment, the method comprises measuring the amount of L-kynurenine, quinolinic acid, and serotonin. An increase in the amount of L-kynurenine and/or quinolinic acid after administration/delivery of the compound or therapy indicates the compound or therapy increases regulatory T cells (Treg) function, activity, frequency, and/or development. A decrease in the amount of serotonin after administration/delivery of the compound or therapy indicates the compound or therapy increases regulatory T cells (Treg) function, activity, frequency, and/or development. In a particular embodiment, the method further comprises detecting and/or measuring the component (e.g., metabolite) of the tryptophan pathway in a corresponding sample prior to administration of the compound or therapy. In a particular embodiment, the method further comprises comparing the amount of the component (e.g., metabolite) of the tryptophan pathway with a standard (e.g., the amount of the component (e.g., metabolite) of the tryptophan pathway detected or measured may be compared to the amount in a corresponding sample from a healthy control (e.g., no neurodegenerative disease, particularly not diagnosed with Parkinson's disease) and/or a control with the neurodegenerative disease). The compound may be any natural or synthetic compound as described hereinbelow (for the neurodegenerative disease treatment). In a particular embodiment, the compound or therapy is a drug or drug candidate. In a particular embodiment, the compound is GM-CSF (e.g., molgramostim or sargramostim), GM-CSF analogs or derivatives, vasoactive intestinal peptide receptor 2 (VIPR2, also known as VPAC2) agonists (e.g., LBT-3627), vasoactive intestinal peptide (VIP), VIP analogs or derivatives, therapeutics causing upregulation of GM-CSF in a patient including but not limited to gene therapies, vaccines, or cell therapies.

In accordance with another aspect the instant invention, methods for determining the efficacy of a neurodegenerative disease treatment (e.g., compound and/or therapy) and/or screening for therapeutic agents for treating, inhibiting, and/or preventing a neurodegenerative disease are provided. In a particular embodiment, the neurodegenerative disease is Parkinson's disease. In a particular embodiment, the method comprises detecting and/or measuring at least one component (e.g., metabolite) of the tryptophan pathway (see, e.g., FIG. 5D) in a sample, particularly a biological sample (e.g., serum or blood), after administration of the neurodegenerative disease treatment to the sample or a subject with said neurodegenerative disease. In a particular embodiment, the method comprises measuring the amount of at least one metabolite selected from the group consisting of L-kynurenine, quinolinic acid, and serotonin. In a particular embodiment, the method comprises measuring the amount of at least two metabolites selected from the group consisting of L-kynurenine, quinolinic acid, and serotonin. In a particular embodiment, the method comprises measuring the amount of L-kynurenine, quinolinic acid, and serotonin. An increase in the amount of L-kynurenine and/or quinolinic acid after administration of the neurodegenerative disease treatment indicates the treatment is inhibiting (decreasing or slowing) and/or treating the neurodegenerative disease. A decrease in the amount of serotonin after administration of the neurodegenerative disease treatment indicates the treatment is inhibiting (decreasing or slowing) and/or treating the neurodegenerative disease. Conversely, a decrease in the amount of L-kynurenine and/or quinolinic acid after administration of the neurodegenerative disease treatment indicates the treatment is ineffective at inhibiting (decreasing or slowing) and/or treating the neurodegenerative disease. An increase in the amount of serotonin after administration of the neurodegenerative disease treatment indicates the treatment is ineffective at inhibiting (decreasing or slowing) and/or treating the neurodegenerative disease. In a particular embodiment, the method further comprises detecting and/or measuring the component (e.g., metabolite) of the tryptophan pathway in a corresponding sample prior to administration of the neurodegenerative disease treatment. In a particular embodiment, the method further comprises comparing the amount of the component (e.g., metabolite) of the tryptophan pathway with a standard (e.g., the amount of the component (e.g., metabolite) of the tryptophan pathway detected or measured may be compared to the amount in a corresponding sample from a healthy control (e.g., no neurodegenerative disease, particularly not diagnosed with Parkinson's disease) and/or a control with the neurodegenerative disease).

The neurodegenerative disease treatment is a may be any natural or synthetic chemical compound (e.g., small molecule compounds (a compound having a molecular weight less than 4,000 atomic mass units (a.m.u.), particularly less than 2,000 a.m.u.), organic or inorganic compounds and molecules, biological macromolecules (such as saccharides, lipids, peptides, proteins, polypeptides and nucleic acid molecules (e.g., those encoding a protein of interest), inhibitory nucleic acid molecule (e.g., antisense, shRNA, miRNA, or siRNA), and drugs (e.g., an FDA approved drug). In a particular embodiment, the neurodegenerative disease treatment is a drug or drug candidate. In a particular embodiment, the neurodegenerative disease treatment is a compound selected from the group consisting of GM-CSF (e.g., molgramostim or sargramostim), GM-CSF analogs or derivatives, vasoactive intestinal peptide receptor 2 (VIPR2, also known as VPAC2) agonists (e.g., LBT-3627), vasoactive intestinal peptide (VIP), VIP analogs or derivatives, therapeutics causing upregulation of GM-CSF in a patient including but not limited to gene therapies, vaccines, or cell therapies. In a particular embodiment, the neurodegenerative disease treatment is a therapy selected from the group consisting of dopamine replacement therapy, a vaccine (e.g., a PD vaccine), and deep brain stimulation (these therapies can be used in the other embodiments described herein).

The markers (e.g., metabolites) of the instant invention may be detected and/or quantitated by any known method. For example, the markers may be detected with proteins such as antibodies which specifically bind the marker (e.g., via Western blot, flow cytometry (e.g., FACS), ELISA, etc.). The antibodies may be conjugated to any detectable agent (e.g., compound or polypeptide) such as isotopes (e.g., radioisotopes), imaging agents, fluorescent agents, and/or contrast agents. In a particular embodiment, a secondary binding ligand, such as a second antibody or a biotin/avidin ligand binding arrangement, which can recognize the primary antibody molecules may be conjugated with the agents described above instead of with the primary antibody. In a particular embodiment, the markers are detected by HPLC or HPLC-MS.

The present invention also encompasses methods for preventing, inhibiting, and/or treating a neurodegenerative disease (e.g., Parkinson's disease). In a particular embodiment, the method comprises administering GM-CSF, particularly sargramostim, to a subject. The GM-CSF, particularly sargramostim, may be delivered in a composition further comprising at least one pharmaceutically acceptable carrier. The composition may also comprise at least one other neurodegenerative disease treatment. The additional neurodegenerative disease treatment may also be administered in a separate pharmaceutical composition from the GM-CSF. The pharmaceutical compositions may be administered at the same time or at different times (e.g., sequentially).

The dosage ranges for the administration of the pharmaceutical compositions of the invention are those large enough to produce the desired effect (e.g., curing, relieving, treating, and/or preventing the neurodegenerative disease, the symptoms of it, or the predisposition towards it). In a particular embodiment, the pharmaceutical composition of the instant invention is administered to the subject at an amount from about 0.1 µg/kg/day to about 500 µg/kg/day, particularly about 0.5 µg/kg/day to about 100 µg/kg/day or about 1 µg/kg/day to about 50 µg/kg/day. The dosage should not be so large as to cause significant adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications.

The compositions of the instant invention may be conveniently formulated for administration with any pharmaceutically acceptable carrier(s). For example, the complexes may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents, or suitable mixtures thereof, particularly an aqueous solution. The concentration of the components in the chosen medium may be varied and the medium may be chosen based on the desired route of administration of the pharmaceutical composition. Except insofar as any conventional media or agent is incompatible with the components to be administered, its use in the pharmaceutical composition is contemplated.

The dose and dosage regimen of compositions of the invention that are suitable for administration to a particular patient may be determined by a physician considering the patient's age, sex, weight, general medical condition, and the specific condition for which the compositions are being administered and the severity thereof. The physician may also take into account the route of administration, the pharmaceutical carrier, and the component's biological activity.

Selection of a suitable pharmaceutical composition will also depend upon the mode of administration chosen. For example, the compositions of the invention may be administered by direct injection or intravenously. In this instance, a pharmaceutical composition comprises the components dispersed in a medium that is compatible with the site of injection.

Compositions of the instant invention may be administered by any method. For example, the compositions of the instant invention can be administered, without limitation parenterally, subcutaneously, orally, topically, pulmonarily, rectally, vaginally, intravenously, intraperitoneally, intrathecally, intracerbrally, epidurally, intramuscularly, intradermally, or intracarotidly. In a particular embodiment, the compositions are administered intramuscularly, subcutaneously, or to the bloodstream (e.g., intravenously). Pharmaceutical compositions for injection are known in the art. If injection is selected as a method for administering the composition, steps must be taken to ensure that sufficient amounts of the components reach their target cells to exert a biological effect. Dosage forms for oral administration include, without limitation, tablets (e.g., coated and uncoated, chewable), gelatin capsules (e.g., soft or hard), lozenges, troches, solutions, emulsions, suspensions, syrups, elixirs, powders/granules (e.g., reconstitutable or dispersible) gums, and effervescent tablets. Dosage forms for parenteral administration include, without limitation, solutions, emulsions, suspensions, dispersions and powders/granules for reconstitution. Dosage forms for topical administration include, without limitation, creams, gels, ointments, salves, patches and transdermal delivery systems.

Compositions of the invention may be formulated in dosage unit form for ease of administration and uniformity of dosage. Dosage unit form, as used herein, refers to a physically discrete unit of the pharmaceutical composition appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. For example, the appropriate dosage unit for the administration of the composition may be determined by evaluating the toxicity of the composition in animal models. Various concentrations of the components in composition may be administered to mice or other mammals, and the minimal and maximal dosages may be determined based on the beneficial results and side effects observed as a result of the treatment.

The compositions of the instant invention may be administered at appropriate intervals until the pathological symptoms are reduced or alleviated, after which the dosage may be reduced to a maintenance level. The appropriate interval in a particular case would normally depend on the condition of the patient.

Definitions

The following definitions are provided to facilitate an understanding of the present invention.

The singular forms "a," "an," and "the" include plural referents unless the context clearly dictates otherwise.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "prevent" refers to the prophylactic treatment of a subject who is at risk of developing a condition (e.g., neurodegenerative disease) resulting in a decrease in the probability that the subject will develop the condition.

A "therapeutically effective amount" of a compound or a pharmaceutical composition refers to an amount effective to prevent, inhibit, treat, or lessen the symptoms of a particular disorder or disease. The treatment of a neurodegenerative disease herein may refer to curing, relieving, and/or preventing the neurodegenerative disease, the symptom(s) of it, or the predisposition towards it.

As used herein, the term "subject" refers to an animal, particularly a mammal, particularly a human.

As used herein, a "biological sample" refers to a sample of biological material obtained from a subject, preferably a human subject, including a tissue, a tissue sample, a cell sample, a tumor sample, and a biological fluid (e.g., blood, urine, or amniotic fluid). In a particular embodiment, the biological sample is blood or serum.

As used herein, "diagnose" refers to detecting and identifying a disease or disorder in a subject. The term may also encompass assessing or evaluating the disease or disorder status (severity, progression, regression, stabilization, response to treatment, etc.) in a patient known to have the disease or disorder.

As used herein, the term "prognosis" refers to providing information regarding the impact of the presence of a disease or disorder (e.g., as determined by the diagnostic methods of the present invention) on a subject's future health (e.g., expected morbidity or mortality). In other words, the term "prognosis" refers to providing a prediction of the probable course and outcome of a disease/disorder or the likelihood of recovery from the disease/disorder.

An "antibody" or "antibody molecule" is any immunoglobulin, including antibodies and fragments thereof, that binds to a specific antigen. As used herein, antibody or antibody molecule contemplates intact immunoglobulin molecules, immunologically active portions of an immunoglobulin molecule, and fusions of immunologically active portions of an immunoglobulin molecule. Antibody fragments include, without limitation, immunoglobulin fragments including, without limitation: single domain (dAb; e.g., single variable light or heavy chain domain), Fab, Fab', F(ab')2, and F(v); and fusions (e.g., via a linker) of these immunoglobulin fragments including, without limitation: scFv, scFv2, scFv-Fc, minibody, diabody, triabody, and tetrabody.

With respect to antibodies, the term "immunologically specific" refers to antibodies that bind to one or more epitopes of a protein or compound of interest, but which do not substantially recognize and bind other molecules in a sample containing a mixed population of antigenic biological molecules.

The following example provides illustrative methods of practicing the instant invention, and is not intended to limit the scope of the invention in any way.

EXAMPLE

Methods
Study Design

Twenty PD patients were recruited from the metropolitan area for an intention to treat design. Inclusion criteria were 35 to 85 years of age at onset with symptoms that included asymmetric bradykinesia and resting tremor or muscle rigidity persisting for ≥3 years, and ≤stage 4 by Hoehn and Yahr disease scale (Goetz et al. (2004) Mov. Disord., 19(9):1020-8). Seventeen age-matched non-parkinsonian subjects served as controls. Exclusion criteria included multiple system atrophy, corticobasal degeneration, unilateral Parkinsonism lasting of >3 years, prior head injury, stroke, brain surgery, a PD family history of >1 blood relative with the disease, mental illness, cognitive impairment, and autoimmune, systemic inflammatory, or hematologic disorders. Patients who received lithium, neuroleptics, immune modulatory treatment within 90 days of study onset, or had allergies to benzyl alcohol, colony stimulating factors, or yeast-derived products were not enrolled. Ferrous metal body implants excluded subjects from magnetoencephalography (MEG) tests.

Randomization and Masking

PD patients were randomized at a 1:1 ratio to receive sargramostim or placebo. Randomization and assignment was performed at the time of accrual since participant enrollment was staggered. Patients were block randomized by the study statistician in randomly chosen blocks of 2 or 4, and the list was given to the trial pharmacist for drug and placebo preparation. The pharmacist prepared identical syringes of sargramostim and placebo to provide doses necessary for two weeks. Examining physicians and medical personnel were blinded to treatment assignment. Randomly-generated three-letter codes identified patient blood samples and were used throughout the study to monitor processing, analyses, and safety.

Procedures

This trial was performed in two parts. In the first part, non-PD controls and PD patients had 3 pre-treatment appointments at −8, −4, and 0 weeks (visits 1-3) to determine a comparative baseline; after which the non-PD controls were dismissed. In the second part beginning at visit 3, PD patients administered by subcutaneous self-injection either sargramostim at 6 μg/kg/day or a placebo of weight-based volume of saline/day for 56 days (Korzenik et al. (2005) N. Engl. J. Med., 352:2193-201). PD patients continued with appointments every 2 weeks for two months (visits 4-7), and a follow-up visit (visit 8) 4 weeks after treatment cessation. Blood samples, physical examinations, and Unified PD Rating Scale Part III (UPDRS III) evaluations were performed during each visit. The primary neurologist performed UPDRS III assessments in a double-blinded fashion in the "ON" state. All but one patient maintained their individually prescribed antiparkinsonian regimen throughout the study.

Study drug was withheld for ~24 hours prior to each visit. White blood cell (WBC) counts with differentials, immunocyte (leukocyte) numbers, and sera metabolites were monitored. Immunocytes obtained from peripheral blood were stained with fluorochrome-conjugated monoclonal antibodies against CD4 (FITC or AF700), CD127 (PerCP-Cy5.5), CD25 (PE), FOXP3/Scurfin (AF647), CD152/CTLA-4 (APC), CD95/FAS/Apo1 (APC), CD39/ENTPD1 (APC), Integrin β7 (APC), (all BD Biosciences, San Jose, Calif.) and CD49d/Integrin α4 (PE-Cy7) (BioLegend Inc., San Diego, Calif.). Isotype-matched antibodies served as negative controls. For FOXP3 and intracellular CTLA4, cells were permeabilized with BD Cytofix/Cytoperm kit (BD Biosciences). Cell surface and intracellular T cell epitopes were examined with an LSR II flow cytometer (BD Biosciences). For Treg function, CD4+CD127loCD25hi cells were enriched by negative selection using a Complete Kit for Human CD4+CD127loCD25+ and CD4+CD127lo enrichment (Stemcell Technologies, Vancouver, Canada). CD25+ Tregs were 89%±8 (mean±SD) of the enriched CD4+ cell population. Naïve CD4+CD25− responder T cells (Tresps) were isolated from healthy donors for proliferation tests (Saunders et al. (2012) J. Neuroimmune. Pharmacol., 7(4):927-38). For T cell gene expression tests, CD4+CD25− T cells were enriched by negative selection on MACS columns (Miltenyi Biotech, San Diego, Calif.). mRNA was isolated from Treg- and Teff-depleted CD4+ T cells, reverse transcribed, and cDNA subjected to real time PCR using the RT2 Profiler Human T Helper Cell Differentiation array (Qiagen, Valencia, Calif.). Fold-changes were determined using the RT2 Profiler PCR array data analysis software version 3.5.

Serum was submitted for antibody and metabolomic profiling. IgG or IgM anti-sargramostim antibodies were screened by ELISA and immunoprecipitation and titers confirmed by endpoint ELISA and by neutralization tests using a luciferase-reported functional assay. For metabolomics, sera was extracted in acetonitrile/methanol, resuspended in acetonitrile/water, sonicated, and analyzed (Deguchi et al. (2015) Blood 126(13):1595-600). Targeted metabolomic analyses employed reverse phase high-performance liquid chromatography-mass spectrometry (HPLC-MS) tests.

Cortical neurophysiological activity during a right-hand movement task was recorded using high-density MEG (Saunders et al. (2012) J. Neuroimmune. Pharmacol., 7(4):927-38). MEG was recorded at 4 weeks (visit 2) before and 8 weeks (visit 7) after initiation of treatment, and 4 weeks (visit 8) after drug cessation. Participants were recorded after 12 hours off parkinsonian medications. MEG data were individually corrected for head motion and noise (Taulu et al. (2006) Phys. Med. Biol., 51(7):1759-68). Artifact-free epochs were transformed into the time-frequency domain, and the movement-related beta event-related desynchronization (ERD) response (14-24 Hz, −300 ms to 200 ms, movement onset=0 ms) was imaged using beamforming (Van Veen et al. (1997) IEEE Trans. Biomed. Eng., 44(9):

867-80; Hillebrand et al. (2005) Hum. Brain Mapp., 25(2): 199-211; Heinrichs-Graham et al. (2014) Cereb. Cortex 24(10):2669-78).

Outcomes

The primary study endpoint was safety as monitored by complete blood counts with differentials, blood metabolic panels, adverse events, and UPDRS part III scores. Hematologic panels were performed by the hospital's clinical laboratory. Regimen-blinded neurologists recorded examinations of blood pressure, pulse, skin, lung, liver, heart, and abdomen, UPDRS III scores were measured in the "ON" state. Adverse events were recorded on treatment diaries by patients and by physicians who rated events by severity (mild, moderate, or severe) and determined whether the event was unrelated, unlikely, possible, probable, or definitely related to the study medication. Moderate events were defined as discomfort, inconvenience, or concerns ameliorated with simple therapeutic measures. Severe adverse events were defined as medically important events that were life threatening, resulted in persistent disability, or required hospitalization. Secondary outcomes were neurophysiological activities as determined by MEG as well as immune phenotype/function and serum profiles from peripheral blood.

Statistical Analyses

Sample size estimates of 16 PD patients and 16 non-PD controls for baseline observations (−8 weeks) were determined to provide 80% power using a two-sided Wilcoxon test assuming normal distribution and a mean percent change from baseline of 0.80. The clinical study yielded an overall mean immune response 6.32 (standard deviation [SD] of 0.97) (Saunders et al. (2012) J. Neuroimmune. Pharmacol., 7(4):927-38). Thus to assess the effects of sargramostim on immune responses in PD patients, a sample size of 8 in each treatment group was determined to provide a 95% CI equal to the sample mean±0.81. All participants that received at least one treatment dose were included in the intention-to-treat design. Statistical analyses were conducted using SAS/STAT software (version 9.2 or higher; SAS Institute Inc., Cary, N.C.) or Statistica (version 9, StatSoft, Tulsa, Okla.), with tests being two-sided. The frequency of adverse events was compared between treatment groups using the Fisher's exact test (Prism, v6, GraphPad Software, Inc., La Jolla, Calif.). CD4+ T cell subsets, function, gene expression, antibody titers, and metabolites were compared between treatment groups using a two independent samples t-test or Mann-Whitney U test. For MEG, a 2×3 mixed-model ANOVA statistical evaluation used peak voxels from each significant brain region with treatment as a between-subjects factor and visit as a repeated factor. For Treg function, percentage inhibition of proliferation was determined at each Treg:Tresp ratio as slope and axis intercepts by linear regression (Prism, v6).

Results

Twenty-two PD patients and seventeen non-parkinsonian subjects to serve as baseline controls were recruited. At the time of enrollment, no significant differences in demographics were discernible between the remaining 20 PD patients and 17 controls (Table 1). PD patients ranged from 53 to 76 years of age with a median and mean age of 64 with symptoms for 3-14 years (median 6 years and mean 7 years). Compared to non-parkinsonian controls, immune and WBC differential profiles for PD patients at entry exhibited increased frequencies of neutrophils and α4β7 integrin-expressing Teffs and Tregs, but decreased levels of CD39+ Tregs and basophils.

TABLE 1

Demographics and entry level values for non-parkinsonian controls and PD patients.

| Demographics[a] | Non-Parkinsonian Controls | | PD Patients | |
| --- | --- | --- | --- | --- |
| Age (yrs) | 17 | 65 (7) | 20 | 64 (7) |
| Time since first symptoms (yr) | n/a | n/a | 20 | 7 (3) |
| Time since diagnosis (yr) | n/a | n/a | 19 | 6 (3) |
| UPDRS-III score | n/a | n/a | 20 | 22 (8) |
| Male Gender | 9 (53) | | 16 (80) | |
| Caucasian Race | 17 (100) | | 20 (100) | |
| Job with Pesticides | 1 (5) | | 2 (10) | |
| Exposure to Pesticides | 4 (24) | | 10 (50) | |
| Job with Chemical Solvents | 4 (24) | | 8 (40) | |
| Job with Other Chemical Fumes | 4 (24) | | 8 (40) | |
| Job with Heavy Metals | 2 (12) | | 2 (10) | |
| Hematological Parameter | | | | |
| WBC ×10$^3$/uL | 6.3 (1.4) | | 6.8 (1.6) | |
| RBC ×10$^6$/uL | 4.7 (0.4) | | 4.7 (0.3) | |
| Hemoglobin g/dL | 14.4 (1.1) | | 14.4 (0.8) | |
| Hematocrit % | 43.2 (6.6) | | 43.1 (2.2) | |
| MCV fL | 91.6 (3.8) | | 91.3 (4.1) | |
| MCHC % | 33.2 (0.9) | | 33.4 (0.7) | |
| RDW % | 13.2 (0.7) | | 13.0 (1.1) | |
| Platelet Count ×10$^3$/uL | 225.6 (37.9) | | 233.0 (57.6) | |
| Neutrophils Relative % | 61.7 (5.6) | | 66.0 (6.9)[b] | |
| Lymphocytes Relative % | 25.4 (6.0) | | 23.2 (5.7) | |
| Monocytes Relative % | 8.5 (1.9) | | 7.4 (1.3) | |
| Eosinophils Relative % | 2.9 (1.5) | | 2.5 (1.4) | |
| Basophils Relative % | 1.0 (0.2) | | 0.7 (0.4)[b] | |
| Neutrophil ×10$^3$/uL | 3.9 (1.0) | | 4.6 (1.2) | |
| Lymphocytes ×10$^3$/uL | 1.6 (0.5) | | 1.6 (0.5) | |
| Monocytes ×10$^3$/uL | 0.5 (0.1) | | 0.5 (0.1) | |
| Eosinophils ×10$^3$/uL | 0.2 (0.1) | | 0.2 (0.1) | |
| Basophils ×10$^3$/uL | 0.1 (0.0) | | 0.0 (0.0) | |
| T Cell Panel | | | | |
| CD3% | 70.5 (7.1) | | 71.3 (8.5) | |
| CD3/uL | 1162.7 (456.9) | | 1123.2 (360.6) | |
| CD4% | 50.9 (7.2) | | 49.2 (11.0) | |
| CD4/uL | 835.9 (320.9) | | 769.4 (263.6) | |
| CD8% | 18.9 (6.4) | | 21.3 (8.1) | |
| CD8/uL | 316.3 (183.2) | | 342.6 (195.6) | |
| CD4/CD8 Ratio | 3.1 (1.0) | | 2.9 (1.1) | |
| % Teff/CD4+ | 1.1 (0.4) | | 1.1 (0.4) | |
| % α4β7 Integrin+/Teff | 8.3 (3.5) | | 14.5 (10.6)[b] | |
| % Treg/CD4+ | 5.4 (1.2) | | 5.4 (1.3) | |
| % FOXP3+/CD4+ | 8.9 (2.8) | | 8.7 (2.6) | |
| % CD39+/Treg | 55.8 (15.8) | | 41.6 (23.8)[c] | |
| % α4β7 Integrin+/Treg | 6.2 (2.1) | | 8.6 (3.0)[b] | |

Data: n, mean (SD); n (%); mean (SD).
[a]Only controls and patients with complete demographic data were used. Information obtained at the time of enrollment.
[b]$p < 0.05$ and
[c]$p < 0.10$ by Mann-Whitney U test.

PD patients randomized to sargramostim or placebo groups (FIG. 1), showed similar demographics and pesticide/heavy metal exposure histories (Table 2). No significant differences in the percentage of patients reporting any adverse event were detected between sargramostim (10/10, 100%, 95% CI 72-100) and placebo treatment groups (8/10, 80%, 95% CI 49-94) (hazard ratio 1.25, 95% CI 0.92-1.70). In sargramostim treated compared to placebo treated patients, the most frequently reported adverse events were injection site reactions (10/10 100% vs. 4/10, 40%, p=0.01), abnormal laboratory/WBC count (10/10, 100% vs. 3/10, 30%, p=0.003), and pain in the upper torso or extremities (7/10, 70% vs. 0/10, 0%, p=0.003); all known to be associated with sargramostim administration (Korzenik et al. (2005) N. Engl. J. Med., 352:2193-201). Eosinophil frequencies increased by 8- to 16-fold during sargramostim treatment (p<0.0001). All hematological values returned to baseline by 4 weeks after drug cessation. Blood metabolic values proved unremarkable during treatment. Adverse event severity was greater in the sargramostim than in the placebo group (p=0.004). The likelihood of a treatment-associated event was greatest in the sargramostim group (p=0.002) with likelihood scores from possible to probable, while those in the placebo group ranged from unlikely to possible. Severe events included a generalized hypersensitivity reaction, a leukocytoclastic vasculitis, and a thrombotic stroke; the latter two deemed unlikely associated with drug. Four sargramostim-treated patients withdrew from the study (FIG. 1, Table 2). In the sargramostim group, levels of serum anti-sargramostim antibodies were detected by week 4 of treatment (visit 5), but diminished by week 8 (visit 7) and were only marginal 4 weeks after the drug was stopped (FIG. 2).

To ensure that sargramostim treatment rendered no untoward effects on motor function, UPDRS III evaluation scores were determined for PD patients and indicated that sargramostim treatment yielded no worsening of motor scores (FIG. 3A). While inter-patient variation precluded an absolute statistical analysis, the scores indicated an overall improvement in sargramostim-treated patients compared to placebo. As a secondary outcome and considering cohort size, changes in normalized scores showed effects of treatment, visit, and treatment-by-visit (FIG. 3B). A transient reduction in score of the placebo group at visit 3 was seen which returned to baseline during the study course. For the sargramostim-treated group, scores diminished throughout the 8-week treatment period by a mean of 3.1±0.5 (p=0.004) compared to 0.5±1.3 (p=0.78) for the placebo group. Notably, the largest reductions in motor severity were observed

TABLE 2

Demographics and adverse events for PD patients randomized to placebo or sargramostim treatment.

| Demographics | Placebo | | Sargramostim | |
|---|---|---|---|---|
| Age (yrs) | 10 | 67 (6) | 10 | 62 (7) |
| Time since first symptoms (yrs) | 9 | 7 (3) | 10 | 7 (2) |
| Time since diagnosis (yrs) | 10 | 5 (4) | 10 | 6 (3) |
| UPDRS III score | 10 | 24 (10) | 10 | 20 (5) |
| Male gender | | 8 (80) | | 8 (80) |
| Caucasian race | | 10 (100) | | 10 (100) |
| Jobs with pesticides | | 3 (30) | | 0 (0) |
| Exposure to pesticides | | 7 (70) | | 3 (30) |
| Jobs with chemical solvents | | 4 (40) | | 4 (40) |
| Jobs with other chemical fumes | | 5 (40) | | 4 (40) |
| Jobs with heavy metals | | 1 (10) | | 1 (10) |
| Adverse Events[a] | | | | |
| Any adverse event | | 8 (80) | | 10 (100) |
| Any severe adverse events | | 0 (0) | | 3 (30) |
| Any serious adverse events | | 0 (0) | | 1 (10) |
| Adverse event leading to withdrawal | | 0 (0) | | 4 (40) |
| Possible relationship to drug | | 7 (70) | | 10 (100) |
| Definitive relationship to drug | | 2 (20) | | 7 (70) |
| Category | | | | |
| Injection site reaction | | 4 (40) | | 10 (100)[b] |
| Abnormal laboratory | | 3 (30) | | 10 (100)[b] |
| Pain, upper torso & extremities | | 0 (0) | | 7 (70)[b] |
| Rash, other than injection site | | 2 (20) | | 4 (40) |
| Chest pain or discomfort | | 0 (0) | | 4 (40) |
| Muscle, soreness, weakness | | 4 (40) | | 3 (30) |
| Pain, lower torso & extremities | | 3 (30) | | 3 (30) |
| Shortness of breath, wheezing | | 0 (0) | | 3 (30) |
| GI tract, nausea, vomiting | | 0 (0) | | 3 (30) |
| Injury | | 3 (30) | | 2 (20) |
| Headache | | 2 (20) | | 2 (20) |
| Fatigue | | 2 (20) | | 2 (20) |
| Infection, any | | 2 (20) | | 2 (20) |
| Neurological, psychological, dyskinesia | | 2 (20) | | 2 (20) |
| Chills, fever | | 1 (10) | | 2 (20) |
| Itching, other than injection site | | 0 (0) | | 2 (20) |
| Cardiovascular, hematological | | 0 (0) | | 2 (20) |
| Skin, not infection | | 3 (30) | | 1 (10) |
| Equilibrium | | 1 (10) | | 1 (10) |
| Sleep anomalies | | 1 (10) | | 1 (10) |
| Edema, other than injection site | | 0 (0) | | 1 (10) |
| Ophthalmological | | 0 (0) | | 1 (10) |
| Severity of adverse events[c] | 1·2 (1·1-1·4) | 1·2 (0·1) | 1·7 (1·4-1·8)[d] | 1·6 (0·3) |
| Likelihood of drug-related[c] | 2·4 (1·9-2·7) | 2·2 (0·6) | 3·8 (3·1-3·9)[d] | 3·6 (0·6) |

Data: n, mean (SD); n (%); median (IQR), mean (SD).
[a]Adverse events reported since the initiation of placebo/drug. More than 2 adverse advents per patient may have been reported. However patients are only counted once within each category. The same patient may be counted in different categories.
[b]$p \leq 0·01$ by Fisher's exact test.
[c]Scored by attending physician.
[d]$p \leq 0·004$ by Mann-Whitney U test.

at 6 and 8 weeks (visits 6 and 7) on sargramostim. Score changes returned to baseline by 4 weeks (visit 8) after treatment cessation.

Decreased beta ERD amplitudes in the motor hand-knob region of the precentral gyrns in PD patients have been shown compared to healthy controls (Saunders et al. (2012) J. Neuroimmune. Pharmacol., 7(4):927-38). No significant differences were found in beta ERD activity in the placebo group (baseline versus on-treatment or on-treatment versus treatment termination) in any motor-related region. In the sargramostim group, beta ERD amplitudes significantly increased from baseline to on-treatment in the left precentral gyrns, right precentral gyrns, right premotor cortex, and supplementary motor area (SMA) ($p<0.005$, cluster-corrected; FIG. 3C, top panel). Notably, each patient exhibited increased beta ERD amplitudes on sargramostim when compared to baseline measures (FIG. 3C, bottom panel).

Frequencies and total numbers of CD3+ T cells were generally increased by sargramostim treatment of PD patients; numbers of CD4+ T cells, but not CD8+ T cells comprised the majority of increased T cell numbers. Frequencies of CD4+ Teffs remained unchanged regardless of regimen (FIG. 4A). In contrast, sargramostim increased frequencies of CD4+CD127loCD25hi Tregs as early as 2 weeks, which remained elevated thereafter. Tregs exhibited higher frequencies of subsets that express CD39 and FAS (CD95), or intracellular CTLA4. The ability to suppress CD3/CD28-stimulated proliferation of Tresps assessed Treg function. Baseline Treg function in PD patients was diminished ($p=0.07$) compared to controls (FIG. 4B). Prior to treatment, Treg function were similar for all groups (FIG. 4B, pretreatment). In contrast, treatment with sargramostim increased Treg activity compared to pretreatment (differences in slopes, $p=0.04$) and to placebo group (differences in slope, $p=0.06$ and elevation, $p=0.07$).

Sargramostim-mediated increases in Treg frequency and function indicated the prevalence of conditions conducive for Treg development. Serum from PD patients prior to, during, and after treatment with sargramostim or placebo was further assessed by global untargeted metabolomic analyses. The findings indicated the involvement of the tryptophan pathway; including metabolites known to regulate inflammation, immunological tolerance and Treg function. Targeted metabolomics for the tryptophan pathway yielded levels of three key metabolites from sargramostim-treated patients that differed significantly from pre- or post-treatment levels and levels from placebo-treated patients (FIGS. 5A and 5D). L-Kynurenine concentration from the sargramostim group was 2.3- and 3.0-fold higher than those from pre- or placebo-treated patients, respectively. Quinolinic acid concentration was 2.4-fold higher than those from either pre- or placebo-treated patients. Both metabolites returned to baseline levels by 4 weeks after treatment. In contrast, serotonin levels from sargramostim-treated patients diminished 2.5-fold ($p=0.03$) and 2.2-fold ($p=0.054$) from levels of pre- and placebo-treated patients.

The presence of both pro- and anti-inflammatory mediators in sargramostim-treated patients posed putative mechanisms for relationships between immunity and clinical outcomes. Thus, the effects of sargramostim on T cell gene expression were examined in a random subset of patients. Six age-matched controls, five placebo-treated and four sargramostim-treated PD patients were evaluated. CD4+ CD25− T cells were isolated from whole blood, RNA was isolated and cDNA made for quantitative real-time PCR to determine expressed genes linked to Th1, Th2, Th17 and Treg. Sargramostim induced a significant upregulation of mRNAs associated with T cell proliferation (GATA4, IL2, HOXA10, and KIF2C) (FIG. 5B). Moreover, with increased Treg numbers and function induced by sargramostim, anti-inflammatory PPARG, LRRC32, FOSL1, IL1R2, IL13RA1, NR4A3, and GFI1 gene expression was increased. Sargramostim up-regulated expression of genes associated with pro-inflammatory Th1 and Th17 effectors (IL17RE, IL17A, RORC, IL18, and EOMES), despite a demonstrated lack of increased Teff numbers in sargramostim-treated patients. These data demonstrate a complex pro- and anti-inflammatory gene expression and network interaction by sargramostim therapy (FIG. 5C).

The administration of sargramostim in PD patients was generally well-tolerated and associated with increases in regulatory T cell numbers, function, and metabolites linked to their induction. Treatment-associated improvements in UPDRS III scores and motor electrical activities paralleled immune changes. The findings indicate that drug-associated polarization of Treg alters brain microenvironment and is responsible for the observed improvements in motor skill activities. This idea is supported further by animal and clinical studies (Benner et al. (2008) PLoS One 3(1): e1376; Reynolds et al. (2010) J. Immunol., 184(5):2261-71; Kosloski et al. (2013) J. Neuroimmunol., 265(1-2):1-10; Saunders et al. (2012) J. Neuroimmune. Pharmacol., 7(4):927-38; Gendelman et al. (2015) J. Neuroimmune. Pharmacol., 10(4):645-50; Mosley et al. (2012) Cold Spring Harb. Perspect. Med., 2(1):a009381). First, nitrated α-synuclein, the dominant protein in dopaminergic neuronal inclusions, induces potent neurotoxic Teffs that accelerate nigrostriatal degeneration (Benner et al. (2008) PLoS One 3(1): e1376; Brochard et al. (2009) J. Clin. Invest., 119(1):182-92). Second, transformation of these Teff responses by Tregs leads to significant dopaminergic neuronal protection (Reynolds et al. (2010) J. Immunol., 184(5):2261-71). Third, proportional change in numbers of interferon-γ-producing Th1, interleukin-4 Th2 and CD4+CD25+ T cells are linked to disease progression. However, whether these PD-associated neuroinflammatory and neurodegenerative immune responses could be harnessed for therapeutic gain was seen only through the present study. Sargramostim-induced changes in T cell profiles affected PD pathobiology. The evidence is bolstered by drug correction of PD-associated Treg dysfunction. Moreover, sargramostim treatment was associated with improved motor task outcomes.

Parallel observations were reported in a spectrum of autoimmune and neurodegenerative diseases (Olson et al. (2016) Curr. Opin. Pharmacol., 26:87-95; Piedavent-Salomon et al. (2015) Brain 138(Pt 11):3263-74; Sheng et al. (2008) Clin. Immunol., 128(2):172-80; Wang et al. (2015) Oncotarget 6(25):20851-62; Ye et al. (2016) J. Neuroinflammation 13(1):10). Treg-mediated abilities to attenuate microglial inflammatory responses and ongoing neurodegeneration are important. Apart from the notable, compensatory Treg activities, proinflammatory Th1 and Th17 T cell and proliferative responses were uncovered. Gene array evaluations showed that sargramostim had multiple effects on peripheral T cells, confirming that an established neuroinflammatory environment was required to affect a regulatory anti-inflammatory profile. This unique idea of cooperative pro- and anti-inflammatory neuroprotection was further supported by metabolomics studies. Here, tryptophan pathway dominance was associated with flow cytometric Treg activity. While 5-hydroxytryptophan is converted to serotonin, tryptophan is, in parallel, converted to kynurenine by indoleamine-pyrrole 2,3-dioxygenase (IDO), and kynurenine is further metabolized to quinolinic acid (Mbongue et al. (2015) Vaccines 3(3):703-29; Hill et al. (2007) Eur. J. Immunol., 37(11):3054-62; Kwidzinski et al. (2007) J. Mol. Med., 85(12):1351-9; Heyes et al. (1997) Biochem. J., 326 (Pt 2):351-6). IDO expression and kynurenine production induce Treg formation. Notably, IDO can be increased by both anti- and pro-inflammatory cytokines as is seen in parkinsonian patients (Munn et al. (2013) Trends Immunol., 34(3): 137-43; Brodacki et al. (2008) Neurosci. Lett., 441(2):158-62).

Sargramostim treatment increased levels of CD3+ and CD4+ T cells, and Tregs (CD4+CD127loCD25hi and CD4+ FoxP3+ T cells) while affecting tryptophan metabolism. Paralleling these immune changes, sargramostim lowered UPDRS-III scores in PD patients, which represent a reduction in motor severity. These findings, taken together, indicate that the effects of sargramostim on T cell polarity change depending on the brain-immune environment. PD is notably driven, in measure, by neuroinflammation and can be corrected. The induction of Treg, modulation of Teff, and overall improvement of immune modulatory activities by Tregs is a novel pathway that corrects aberrant immune responses during PD.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of determining the efficacy of a Parkinson's disease treatment, said method comprising:
    a) administering the Parkinson's disease treatment to a subject having Parkinson's disease, wherein said Parkinson's disease treatment is sargramostim; and
    b) measuring the amount of at least one metabolite of the tryptophan pathway in a biological sample obtained from the subject after step a),
    wherein at least one of the metabolites measured in step b) is L-kynurenine, quinolinic acid, or serotonin, and
    wherein an increase in the amount of L-kynurenine or quinolinic acid after administration of the Parkinson's disease treatment indicates the Parkinson's disease treatment is effective against Parkinson's disease or wherein a decrease in the amount of serotonin after administration of the Parkinson's disease treatment indicates the Parkinson's disease treatment is effective against Parkinson's disease; and
    c) treating said subject with sargramostim when the Parkinson's disease treatment is effective against Parkinson's disease.

2. The method of claim 1, wherein step b) comprises measuring L-kynurenine, quinolinic acid, and serotonin.

3. The method of claim 1, wherein said biological sample is blood or serum.

4. The method of claim 1, wherein step b) comprises measuring at least two metabolites selected from the group consisting of L-kynurenine, quinolinic acid, and serotonin.

* * * * *